United States Patent
Sawai et al.

(10) Patent No.: US 11,597,694 B2
(45) Date of Patent: *Mar. 7, 2023

(54) METHOD FOR PRODUCING LACTIC ACID AND METHOD FOR PRODUCING POLYLACTIC ACID

(71) Applicant: Toray Industries, Inc., Tokyo (JP)

(72) Inventors: Kenji Sawai, Kamakura (JP); Hideki Sawai, Kamakura (JP); Takashi Mimitsuka, Kamakura (JP); Masateru Ito, Kamakura (JP); Katsushige Yamada, Kamakura (JP); Kenji Kawamura, Kamakura (JP); Shin-ichi Minegishi, Otsu (JP); Izumi Nakagawa, Kamakura (JP); Tatsuya Nagano, Nagoya (JP)

(73) Assignee: Toray Industries, Inc., Tokyo (JP)

( * ) Notice: Subject to any disclaimer, the term of this patent is extended or adjusted under 35 U.S.C. 154(b) by 435 days.

This patent is subject to a terminal disclaimer.

(21) Appl. No.: 15/931,772

(22) Filed: May 14, 2020

(65) Prior Publication Data

US 2020/0325097 A1 Oct. 15, 2020

Related U.S. Application Data

(63) Continuation of application No. 13/142,062, filed as application No. PCT/JP2009/071572 on Dec. 25, 2009, now Pat. No. 10,683,254.

(30) Foreign Application Priority Data

Dec. 26, 2008 (JP) .................................. 2008-333014
Dec. 26, 2008 (JP) .................................. 2008-333015

(51) Int. Cl.
| | | |
|---|---|---|
| *C07C 59/08* | (2006.01) | |
| *B01D 71/56* | (2006.01) | |
| *C07C 51/42* | (2006.01) | |
| *C08G 63/06* | (2006.01) | |
| *C12P 7/56* | (2006.01) | |
| *B01D 61/02* | (2006.01) | |

(52) U.S. Cl.
CPC ............ *C07C 59/08* (2013.01); *B01D 61/027* (2013.01); *B01D 71/56* (2013.01); *C07C 51/42* (2013.01); *C08G 63/06* (2013.01); *C12P 7/56* (2013.01); *B01D 2311/04* (2013.01); *B01D 2311/06* (2013.01); *B01D 2311/18* (2013.01); *B01D 2311/2669* (2013.01); *B01D 2311/2688* (2013.01); *C07B 2200/07* (2013.01)

(58) Field of Classification Search
CPC . C07C 51/42; C07C 59/08; C12P 7/56; B01D 2311/04; B01D 2311/06; B01D 2311/18; B01D 2311/2669; B01D 2311/2688; B01D 61/027; B01D 71/56; C07D 319/12; C07B 2200/07; C08G 63/06; C08G 63/08

See application file for complete search history.

(56) References Cited

U.S. PATENT DOCUMENTS

| | | |
|---|---|---|
| 4,857,363 A | 8/1989 | Sasaki et al. |
| 5,444,143 A | 8/1995 | Ohta et al. |
| 5,503,750 A | 4/1996 | Russo, Jr. et al. |
| 5,681,728 A | 10/1997 | Miao |
| 6,489,508 B1 | 12/2002 | Van Gansbeghe et al. |
| 10,683,254 B2 * | 6/2020 | Sawai ..................... C07C 59/08 |
| 2002/0004611 A1 | 1/2002 | Eyal et al. |
| 2002/0177199 A1 | 11/2002 | Hames et al. |
| 2004/0033573 A1 | 2/2004 | Norddahl et al. |
| 2005/0222379 A1 | 10/2005 | Matsuo et al. |
| 2008/0254165 A1 | 10/2008 | Patel et al. |
| 2009/0269812 A1 | 10/2009 | Sawai et al. |
| 2010/0062503 A1 | 3/2010 | Visser et al. |

FOREIGN PATENT DOCUMENTS

| | | |
|---|---|---|
| CN | 101306993 | 11/2008 |
| EP | 1060785 | 12/2000 |
| GB | 907321 | 10/1962 |
| JP | 56-065841 A | 6/1981 |

(Continued)

OTHER PUBLICATIONS

European Search Report dated Jan. 31, 2017, of corresponding European Application No. 16196147.9.

Bhattacharyya, S.K., "Catalytic Synthesis of Lactic Acid from Acetaldehyde, Carbon Monoxide, and Water," *Industrial & Engineering Chemistry Product Research and Development*, vol. 9, No. 1, Mar. 1, 1970, pp. 92-95.

Anonymous, "Galacid Industrial 90 Ultra-Pure," *Galactic*, URL: XP002765964, https://www.lactic.com/downlods/filter.ashx?file=Specs/LAIUL90.pdf, retrieved on Jan. 9, 2017.

(Continued)

*Primary Examiner* — Susan M Hanley

(74) *Attorney, Agent, or Firm* — DLA Piper LLP (US)

(57) ABSTRACT

Lactic acid is obtained by a method including (A) a step of continuous fermentation wherein a fermentation culture medium of a microorganism having an ability of lactic acid fermentation is filtered through a porous membrane having an average pore size of not less than 0.01 μm and less than 1 μm with a transmembrane pressure difference within the range of 0.1 to 20 kPa, and the permeate is collected, while retaining the non-permeated liquid in or returning the non-permeated liquid to the culture, and adding a fermentation feedstock to the culture; (B) a step of filtering the permeate obtained in Step (A) through a nanofiltration membrane; and (C) a step of distilling the permeate obtained in Step (B) under a pressure of not less than 1 Pa and not more than atmospheric pressure, at 25° C. to 200° C. to recover lactic acid.

6 Claims, 3 Drawing Sheets

Specification includes a Sequence Listing.

(56) References Cited

FOREIGN PATENT DOCUMENTS

| | | |
|---|---|---|
| JP | 57-082340 A | 5/1982 |
| JP | 62-72646 | 4/1987 |
| JP | 62-201606 A | 9/1987 |
| JP | 63-290840 A | 11/1988 |
| JP | 6-279577 A | 10/1994 |
| JP | 7-133344 A | 5/1995 |
| JP | 8-188642 A | 7/1996 |
| JP | 9-031170 A | 2/1997 |
| JP | H09-121844 | 5/1997 |
| JP | H09-121877 | 5/1997 |
| JP | 2001-506274 T | 5/2001 |
| JP | 2001-258584 A | 9/2001 |
| JP | 2002-300898 A | 10/2002 |
| JP | 2005-270025 A | 10/2005 |
| JP | 2006-137892 A | 6/2006 |
| JP | 2008-029329 A | 2/2008 |
| JP | 2008-048726 A | 3/2008 |
| WO | 00/56693 | 9/2000 |
| WO | 01/92555 A1 | 12/2001 |
| WO | 2004/057008 A1 | 7/2004 |
| WO | 2007/010548 | 1/2007 |
| WO | 2007/097260 A1 | 8/2007 |

OTHER PUBLICATIONS

Vijayakumar, J., et al., "Recent Trends in the Production, Purification and Application of Lactic Acid," *Chemical and Biochemical Engineering Quarterly*, vol. 22, No. 2, Jun. 1, 2008, pp. 245-264.

Chinese Office Action dated Sep. 5, 2016, of corresponding Chinese Application No. 201510690871.5 with an English translation.

European Search Report dated Feb. 14, 2018, of corresponding European Application No. 16196147.9.

Zhou, S. et al., "Production of Optically Pure D-Lactic Acid in Mineral Salts Medium by Metabolically Engineered *Escherichia coli* W3110," *Applied and Environmental Microbiology*, Jan. 2003, vol. 69, No. 1, pp. 399-407.

Okino, S. et al., "Production of D-Lactic Acid by *Corynebacterium glutamicum* under Oxygen Deprivation," *Applied Microbiology and Biotechnology*, Jan. 2008, vol. 78, No. 1, pp. 449-454.

\* cited by examiner

```
                          SEQUENCE LISTING

<160> NUMBER OF SEQ ID NOS: 11

<210> SEQ ID NO 1
<211> LENGTH: 999
<212> TYPE: DNA
<213> ORGANISM: Xenopus laevis

<400> SEQUENCE: 1
atggcaactg tgaaggataa actcatccac aatgtggtca aggaggagtc gctcccccag    60
aacaaggtca ccattgtggg tgtggggggcc gtgggcatgg cctgtgccat cagtgtcctg   120
cagaaggatt tggcagatga gcttgcactt gttgatgtga tagaagacaa actgaagggg   180
gaaatgatgg atctccagca tggcagtctg ttccttcgta cccccaagat tgtctcaggg   240
aaagattaca gcgtcactgc aaactccaag ctggtagttg tgacggccgg ggcccgtcag   300
caggagggag agagtcgcct gaatctggtt cagcgcaatg tcaacatctt caaattcatc   360
attcccaaca ttgtcaagta cagccccaac tgcaccctgc tcatcgtctc caacccagtg   420
gacattctga catatgtggc ctggaagatc agtggattcc ccaaaaaccg tgtcattggc   480
agcggctgca atttggactc tgcccgtttc cgttacctca tggggcagaa gtttgggatc   540
cacacccaga gctgccacgg ttgggtcatt ggggaacacg gagactcgag tgtgccagtg   600
tggagtgggg tgaatgtggc tggcgtgtcc ctgaaaaccc tgcacccccga tattgggagt   660 gacgcagaca aggagaactg gaaggaggtg cacaagcagg ttgtggacag cgcctatgaa   720
gtgatcaagc tgaagggcta cacctcctgg gctattggcc tgtccgtagc tgacctgtct   780
gagagtatcc tgaagaacct ccgccgagtc catcccattt ccacaatggt caagggcatg   840
tacggcgtga ataatgatgt tttcctcagt gtccccctgtg tgtttgggcaa cttgggcatc   900 acagacgtgg ttaacatgac gctgaaggca gatgaagagg atcgcttacg caagagcgca   960
gacaccctgt gggccatcca gaaggagctg cagttctag                          999

<210> SEQ ID NO 2
<211> LENGTH: 85
<212> TYPE: DNA
<213> ORGANISM: Artificial
<220> FEATURE:
<223> OTHER INFORMATION: primer

<400> SEQUENCE: 2
tattgattta tagtcgtaac tacaaagaca agcaaaataa aatacgttcg ctctattaag    60
atggcaactg tgaaggataa actca                                         85

<210> SEQ ID NO 3
<211> LENGTH: 20
<212> TYPE: DNA
<213> ORGANISM: Artificial
<220> FEATURE:
<223> OTHER INFORMATION: primer

<400> SEQUENCE: 3
aggcgtatca cgaggccctt                                               20

<210> SEQ ID NO 4
```

```
<211> LENGTH: 60
<212> TYPE: DNA
<213> ORGANISM: Artificial
<220> FEATURE:
<223> OTHER INFORMATION: primer

<400> SEQUENCE: 4
gaattaattc ttgaagacga aagggcctcg tgatacgcct agattgtact gagagtgcac    60

<210> SEQ ID NO 5
<211> LENGTH: 80
<212> TYPE: DNA
<213> ORGANISM: Artificial
<220> FEATURE:
<223> OTHER INFORMATION: primer

<400> SEQUENCE: 5
aaaaaataac ataatactga agaaaagcat taagaaggcg gatgtgtcaa acaccaccgt    60
ctgtgcggta tttcacaccg                                                80

<210> SEQ ID NO 6
<211> LENGTH: 20
<212> TYPE: DNA
<213> ORGANISM: Artificial
<220> FEATURE:
<223> OTHER INFORMATION: primer

<400> SEQUENCE: 6
tagattggcc gtaggggctg                                                20

<210> SEQ ID NO 7
<211> LENGTH: 20
<212> TYPE: DNA
<213> ORGANISM: Artificial
<220> FEATURE:
<223> OTHER INFORMATION: primer

<400> SEQUENCE: 7
cacgcaacgc gtaagaaaca                                                20

<210> SEQ ID NO 8
<211> LENGTH: 24
<212> TYPE: DNA
<213> ORGANISM: Artificial
<220> FEATURE:
<223> OTHER INFORMATION: primer

<400> SEQUENCE: 8
gacaattctg gttaggtcca agag                                           24

<210> SEQ ID NO 9
<211> LENGTH: 24
<212> TYPE: DNA
<213> ORGANISM: Artificial
<220> FEATURE:
<223> OTHER INFORMATION: primer

<400> SEQUENCE: 9
ttaagctgct gcggagcttc cacg                                           24

<210> SEQ ID NO 10
<211> LENGTH: 22
<212> TYPE: DNA
<213> ORGANISM: Artificial
<220> FEATURE:
<223> OTHER INFORMATION: primer
```

-continued

```
<400> SEQUENCE: 10
atgtctgccc ctaagaagat cg                                              22

<210> SEQ ID NO 11
<211> LENGTH: 24
<212> TYPE: DNA
<213> ORGANISM: Artificial
<220> FEATURE:
<223> OTHER INFORMATION: primer

<400> SEQUENCE: 11
ttaagcaagg attttcttaa cttc                                            24
```

METHOD FOR PRODUCING LACTIC ACID AND METHOD FOR PRODUCING POLYLACTIC ACID

TECHNICAL FIELD

This disclosure relates to a method for producing lactic acid, in which a microorganism having an ability of lactic acid fermentation is cultured and lactic acid produced in the obtained fermentation broth is separated, and a method for producing a polylactic acid using the lactic acid obtained by the method for producing lactic acid. The disclosure also relates to the lactic acid and the polylactic acid obtained by these production methods.

BACKGROUND

Lactic acid is widely used for food, pharmaceuticals and the like, and also widely applied to industrial uses as a monomer material for polylactic acid, which is a biodegradable plastic, so that its demand is increasing. Lactic acid is known to be produced by fermentation by microorganisms which convert carbohydrate-containing substrates represented by glucose into lactic acid.

To obtain lactic acid as a raw material for polylactic acid, a highly productive production method of lactic acid is required since the necessary amount of lactic acid is large. To enhance productivity of lactic acid, a high yield relative to sugar consumption in the microbial fermentation as well as a high production rate of lactic acid per unit time per unit volume are indispensable and, in WO 2007/097260, a method of enhancement of the production rate by a culture apparatus using a porous membrane is disclosed.

A polylactic acid can be produced by a method by ring-opening polymerization of lactide, which is a cyclic dimer of lactic acid, or a method by direct polymerization of a raw material lactic acid. In the lactide method, lactic acid is once oligomerized and then depolymerized while isolating lactide produced, which is then subjected to ring-opening polymerization in the presence of a catalyst. In this method, the polymerization process is complicated and, hence, requires much labor and cost. Since, in this process, impurities in the raw material lactic acid can be removed by the operation of lactide isolation, a raw material lactic acid of relatively low quality can be used. However, since impurities in the raw material lactic acid, such as inorganic ions, cause decrease in the yield of lactide to be isolated, the raw material lactic acid needs to be relatively free from impurities. On the other hand, in the direct polymerization method, the raw material lactic acid is subjected to direct dehydration polycondensation in the presence of a catalyst. In this method, simplification of the process can be expected compared to the lactide method, but impurities that inhibit the polymerization need to be preliminarily removed from the raw material lactic acid, to provide a high-quality raw material lactic acid. Thus, the purification efficiency of lactic acid influences the enhancement of productivity of lactide and polylactic acid.

Production of lactic acid by microbial fermentation is carried out while adding an alkaline substance to the culture medium to maintain the optimum pH for the microbial fermentation, and examples of the alkaline substance to be added to the culture medium include calcium hydroxide. In cases where calcium hydroxide was used, the lactic acid produced by microbial fermentation exists in the culture medium as calcium lactate. By adding an acidic substance (e.g., sulfuric acid) to the culture medium after completion of the culture, a solution of free lactic acid can be obtained, but a calcium salt (e.g., calcium sulfate) is by-produced as an impurity.

As a method for separating lactic acid by removing the by-produced calcium salt, in cases where an insoluble calcium salt such as calcium sulfate precipitates, a method by filtration through qualitative filter paper or the like is used, but a small amount of the calcium salt dissolved in the solution cannot be removed, and remains in the lactic acid-containing solution. Therefore, in cases where this filtrate containing lactic acid is, for example, concentrated in a later purification step, the calcium salt and other soluble inorganic acids deposit (precipitate) in the solution containing free lactic acid, which has been problematic. It is known that, if the lactic acid-containing solution from which inorganic ions have not been sufficiently removed is heated by an operation such as distillation, the inorganic ions allow racemization and oligomerization of lactic acid to proceed.

Examples of the method of removal of small amounts of inorganic ions from a lactic acid-containing solution include methods using ion-exchange resins (e.g., see Japanese Translated PCT Patent Application Laid-Open No. 2001-506274). However, to maintain the ion-exchange performance of the ion-exchange resin, the ion-exchange resin must be regenerated periodically. Further, since regeneration of an ion-exchange resin is carried out by using large amounts of an aqueous sodium hydroxide solution and an aqueous hydrochloric acid solution, a large amount of waste fluid is discharged during the regeneration, so that a large amount of cost is required for waste liquid disposal, which has been problematic. Further, repeated regeneration of an ion-exchange resin results in decrease in the regeneration rate of the ion-exchange resin, as well as decrease in the ion-exchange performance, leading to decrease in the removal rate of inorganic acids, which have been problematic.

Further, methods of removal of small amounts of inorganic ion components such as calcium components from a lactic acid-containing solution using an electrodialyzer with a bipolar membrane are also known (e.g., see JP 2005-270025 A). However, the bipolar membrane used in these methods is expensive and the efficiency of removal of inorganic salts such as calcium salts is not necessarily high, which have been problematic.

Further, methods of removal of inorganic salts from a lactic acid-containing solution using a nanofiltration membrane have been disclosed (e.g., see U.S. Pat. Nos. 5,503,750, 5,681,728 and US 2004/0033573). However, a step of recovery of lactic acid by distillation, the effect of distillation on the yield of lactic acid, and the possibility of application of the obtained lactic acid to industrial-scale production of a polylactic acid by direct polymerization have not been disclosed.

Further, in JP 6-279577 A, JP 7-133344 A, JP 8-188642 A and JP 9-31170 A, the fact that the amounts of particular impurities need to be less than particular levels to obtain a high-molecular-weight polylactic acid has been disclosed, but the influences of impurities on the thermal stability, mechanical strength and hue, which are important factors for the processability of polylactic acids, have not been disclosed.

It could therefore be helpful to provide a method for producing lactic acid with high productivity, which lactic acid can be applied to industrial-scale production of a polylactic acid by direct polymerization and can be used for high-yield synthesis of lactide; and methods for producing lactide and a polylactic acid using the lactic acid. Further, it could be helpful to provide a polylactic acid having excellent thermal stability, mechanical strength and hue, and to provide lactic acid in which the amounts of specific impurities are not more than certain amount, and lactide and a polylactic acid obtained using the lactic acid as a raw material.

SUMMARY

We discovered that culturing of a microorganism having an ability to produce lactic acid in a continuous culture apparatus using a porous membrane enables to obtain lactic acid in the permeate at a high yield and at a high production rate, and, by providing the obtained permeate for a nanofiltration step and a distillation step, lactic acid which is applicable to direct polymerization and allows high-yield synthesis of lactide can be obtained. We also discovered that, by using lactic acid, in which the amounts of particular impurities are not more than particular levels, as a raw material for a polylactic acid, lactide having excellent hue and a polylactic acid having excellent thermal stability, mechanical strength and hue can be obtained at high yields.

We thus provide:
(1) A method for producing lactic acid, the method comprising the Steps (A) to (C) below:
  (A) a step of continuous fermentation wherein a fermentation culture medium of a microorganism having an ability of lactic acid fermentation is filtered through a porous membrane having an average pore size of not less than 0.01 μm and less than 1 μm with a transmembrane pressure difference within the range of 0.1 to 20 kPa, and the permeate is collected, while retaining the non-permeated liquid in or returning the non-permeated liquid to the culture medium, and adding a fermentation feedstock to the culture medium;
  (B) a step of filtering the permeate obtained in Step (A) through a nanofiltration membrane; and
  (C) a step of distilling the permeate obtained in Step (B) under a pressure of not less than 1 Pa and not more than atmospheric pressure, at not less than 25° C. and not more than 200° C. to recover lactic acid.
(2) A method for producing lactic acid according to (1), wherein the pH of the permeate obtained in the Step (A) is adjusted to not less than 2 and not more than 4.5, followed by providing the permeate for the Step (B).
(3) The method for producing lactic acid according to (1) or (2), wherein the Step (A) is a step of continuous fermentation in the presence of a calcium salt, and a solution containing lactic acid obtained after Step (D), in which the calcium component in the permeate obtained in the Step (A) is removed as an insoluble sulfate, is provided for the Step (B).
(4) The method for producing lactic acid according to any one of (1) to (3), wherein the ratio of the permeation rate of magnesium sulfate relative to the permeation rate of citric acid through the nanofiltration membrane is not less than 3 at an operation pressure of 0.5 MPa, raw liquid temperature of 25° C. and concentration in the raw liquid of 1000 ppm.
(5) The method for producing lactic acid according to any one of (1) to (4), wherein the permeation rate of magnesium sulfate through the nanofiltration membrane is not more than 1.5% at an operation pressure of 0.5 MPa, raw liquid temperature of 25° C. and concentration in the raw liquid of 1000 ppm.
(6) The method for producing lactic acid according to any one of (1) to (5), wherein the membrane material of the nanofiltration membrane comprises a polyamide.
(7) The method for producing lactic acid according to (6), wherein the polyamide comprises a cross-linked piperazine polyamide as a major component and further comprises a constituting component represented by Formula 1:

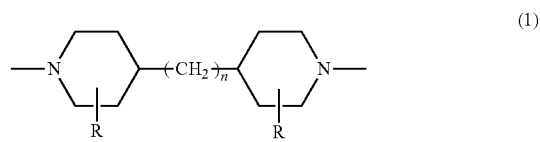

wherein R represents —H or —CH$_3$; and n represents an integer of 0 to 3.
(8) A method for producing lactide, wherein lactic acid obtained by the method for producing lactic acid according to any one of (1) to (7) is used as a raw material.
(9) A method for producing a polylactic acid, wherein lactide obtained by the method for producing lactide according to (8) is polymerized.
(10) A method for producing a polylactic acid, wherein lactic acid obtained by the method for producing lactic acid according to any one of (1) to (7) is polymerized by direct dehydration polycondensation.
(11) Lactic acid whose 90% aqueous solution contains methanol at a concentration of not more than 70 ppm, pyruvic acid at a concentration of not more than 500 ppm, furfural at a concentration of not more than 15 ppm, 5-hydroxymethylfurfural at a concentration of not more than 15 ppm, methyl lactate at a concentration of not more than 600 ppm, acetic acid at a concentration of not more than 500 ppm and 2-hydroxybutyric acid at a concentration of not more than 500 ppm.
(12) The lactic acid according to (11), having an optical purity of not less than 90%.
(13) Lactide obtained by using the lactic acid according to (11) or (12) as a raw material.
(14) A polylactic acid obtained by using the lactic acid according to (11) or (12) or the lactide according to (13) as a raw material.
(15) A polylactic acid obtained by direct dehydration polycondensation using the lactic acid according to (11) or (12) as a raw material.

High-quality lactic acid can be produced, and the productivity of a polylactic acid, which is a biodegradable general-purpose plastic, can be improved. Further, by using lactic acid, in which the amounts of specific impurities are not more than certain amount, as a raw material for a polylactic acid, a polylactic acid having excellent thermal stability, mechanical strength and hue can be obtained.

DESCRIPTION OF SYMBOLS

Figure 1:
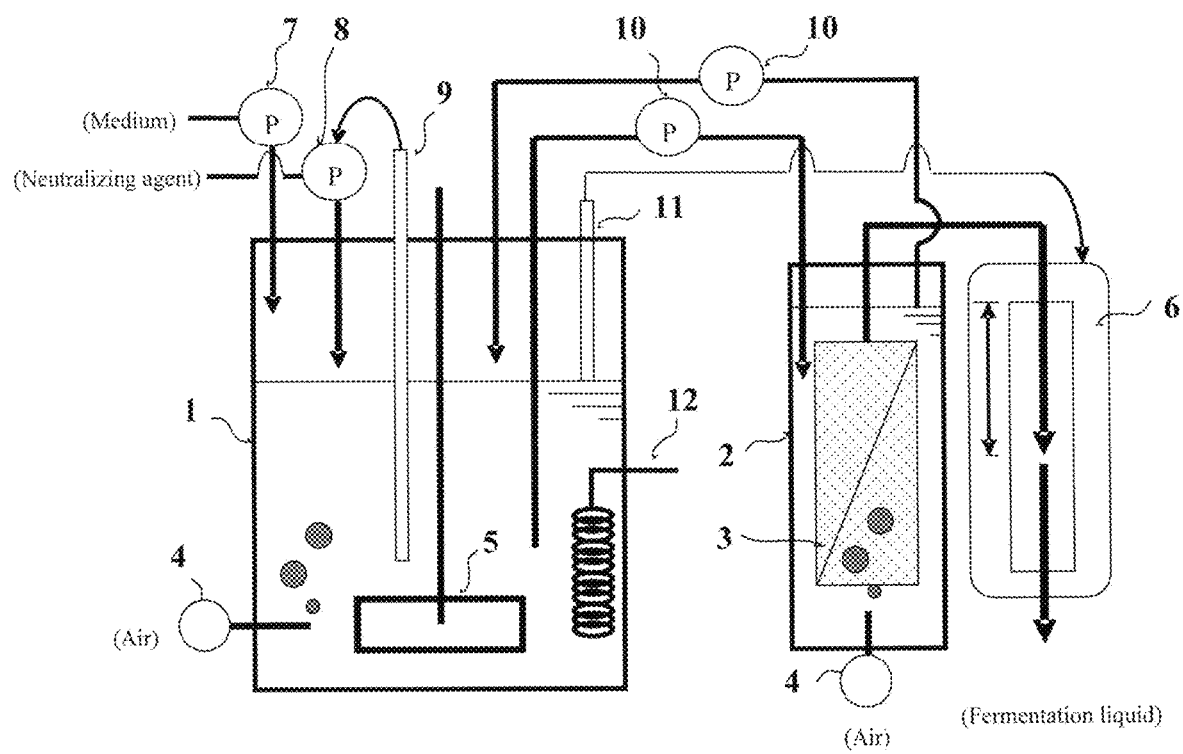
FIG. 1 is a schematic diagram showing an example of the continuous culture apparatus.

1. Fermentation reactor
2. Membrane separation vessel
3. Separation membrane element
4. Gas supplying apparatus
5. Stirrer
6. Hydraulic head difference controlling apparatus
7. Culture medium supplying pump
8. pH adjustment solution supplying pump
9. pH sensor/controlling apparatus
10. Fermentation liquid circulating pump
11. Level sensor
12. Temperature controller
13. Raw liquid tank
14. Cell equipped with nanofiltration membrane or reverse osmosis membrane
15. High-pressure pump
16. Flow of membrane permeate
17. Flow of membrane concentrate
18. Flow of culture medium sent by high-pressure pump
19. Nanofiltration membrane
20. Supporting plate

DETAILED DESCRIPTION

Our methods will now be described in more detail.

Method of Production of Lactic Acid

The method of production of lactic acid comprises the Steps (A) to (C) below:

(A) a step of continuous fermentation wherein a fermentation culture medium of a microorganism having an ability of lactic acid fermentation is filtered through a porous membrane having an average pore size of not less than 0.01 µm and less than 1 µm with a transmembrane pressure difference within the range of 0.1 to 20 kPa, and the permeate is collected, while retaining the non-permeated liquid in or returning the non-permeated liquid to the culture medium, and adding a fermentation feedstock to the culture medium;

(B) a step of filtering the permeate obtained in Step (A) through a nanofiltration membrane; and (C) a step of distilling the solution obtained in Step (B) under a pressure of not less than 1 Pa and not more than atmospheric pressure, at not less than 25° C. and not more than 200° C. to recover lactic acid.

The microorganism having an ability of lactic acid fermentation which is used in Step (A) will now be described. The microorganism having an ability of lactic acid fermentation is not restricted as long as it can produce lactic acid, and a lactic acid bacterium or a microorganism to which an ability of lactic acid fermentation was artificially given or whose ability of lactic acid fermentation was enhanced may be preferably used.

The lactic acid bacterium may be defined herein as a prokaryotic microorganism which produces lactic acid with an yield of not less than 50% relative to glucose consumed. Preferred examples of the lactic acid bacterium include those belonging to the genus *Lactobacillus*, genus *Pediococcus*, genus *Tetragenococcus*, genus *Carnobacterium*, genus *Vagococcus*, genus *Leuconostoc*, genus *Oenococcus*, genus *Atopobium*, genus *Streptococcus*, genus *Enterococcus*, genus *Lactococcus*, genus *Sporolactobacillus* and genus *Bacillus*. By selecting, among these, a lactic acid bacterium showing a high yield of lactic acid relative to sugar consumption, the bacterium can be preferably used in the production of lactic acid. Further, by selecting a lactic acid bacterium showing a high yield of L-lactic acid or D-lactic acid relative to sugar consumption, the bacterium can be preferably used in production of lactic acid having a high optical purity.

Examples of the lactic acid bacterium showing a high yield of L-lactic acid relative to sugar consumption include *Lactobacillus yamanashiensis, Lactobacillus animalis, Lactobacillus agilis, Lactobacillus aviaries, Lactobacillus casei, Lactobacillus delbruekii, Lactobacillus paracasei, Lactobacillus rhamnosus, Lactobacillus ruminis, Lactobacillus salivarius, Lactobacillus sharpeae, Pediococcus dextrinicus* and *Lactococcus lactis*, which may be selected and used for production of L-lactic acid.

Examples of the lactic acid bacterium showing a high yield of D-lactic acid relative to sugar consumption include *Sporolactobacillus laebolacticus, Sporolactobacillus inulinus, Lactobacillus bulgaricus, Lactobacillus casei, Lactobacillus delbruekii* and *Lactococcus lactis*, which may be selected and used for production of D-lactic acid.

Examples of the microorganism to which an ability of lactic acid fermentation was artificially given or whose ability of lactic acid fermentation was enhanced include microorganisms obtained by known chemical mutagenesis and microorganisms to which a lactate dehydrogenase (which may be hereinafter referred to as LDH) gene was introduced to give or enhance an ability of lactic acid fermentation. Preferred examples thereof include recombinant microorganisms to which LDH was incorporated intracellularly to enhance an ability of lactic acid fermentation.

Preferred examples of the host of the recombinant microorganisms include prokaryotic cells such as *E. coli* and lactic acid bacteria; and eukaryotic cells such as yeast; and the host is more preferably yeast. The yeast preferably belongs to the genus *Saccharomyces*, and the yeast is more preferably *Saccharomyces cerevisiae*.

The LDH gene is not restricted as long as it encodes a protein having an activity to convert reduced nicotinamide adenine dinucleotide (NADH) and pyruvic acid to oxidized nicotinamide adenine dinucleotide (NAD+) and lactic acid. For example, an L-LDH gene derived from a lactic acid bacterium showing a high yield of L-lactic acid relative to sugar consumption, or a D-LDH gene derived from a lactic acid bacterium showing a high yield of D-lactic acid relative to sugar consumption may be used. Further, preferred examples of the L-LDH gene include those derived from eukaryotes such as cow, human and frog, and the L-LDH gene is more preferably derived from *Xenopus laevis*. Examples of microorganisms to which an L-LDH gene derived from a frog is incorporated include the recombinant yeast disclosed in JP 2008-029329 A.

Examples of the LDH gene also include variants due to genetic polymorphisms and mutagenesis. The term "genetic polymorphism" means partial modification of the base sequence of a gene due to natural mutation occurred in the gene. The term "mutagenesis" means artificial introduction of a mutation into a gene. Examples of the method of mutagenesis include a method using a site-directed mutagenesis kit (Mutan-K (manufactured by TAKARA BIO INC.)) and a method using a random mutagenesis kit (BD Diversify PCR Random Mutagenesis (manufactured by CLONTECH)). The LDH may have a deletion(s) and/or insertion(s) in a part of its base sequence as long as it encodes a protein having an activity to convert NADH and pyruvic acid to NAD+ and lactic acid.

The porous membrane used in Step (A) will now be described. The porous membrane used as a separation membrane is preferably less prone to clogging by the microorganism having an ability of lactic acid fermentation, and has a property to stably maintain the filtration performance for a long time. Therefore, it is important for the porous membrane to have an average pore size of not less than 0.01 µm and less than 1 µm. The porous membrane has a separation performance and a permeability suitable for the properties and the use of the liquid to be processed and, in view of the blocking performance, permeability and resistance to dirt, which affects the separation performance, the porous membrane is preferably one having a porous resin layer. As the porous membrane having a porous resin layer, one having a porous resin layer on the surface of a porous base material, which layer acts as a separation function layer, is preferred. The porous base material supports the porous resin layer to strengthen the porous membrane.

The porous base material is composed of an organic material, inorganic material and/or the like, and an organic fiber is preferably used. Preferred examples of the porous base material include woven fabrics and non-woven fabrics prepared using organic fibers such as cellulose fibers, cellulose triacetate fibers, polyester fibers, polypropylene fibers and polyethylene fibers, among which non-woven fabrics are preferably used since their densities can be relatively easily controlled, they can be simply produced, and they are inexpensive.

As the porous resin layer, which acts as a separation functional layer as mentioned above, an organic polymer membrane may be suitably used. Examples of the material of the organic polymer membrane include polyethylene resins, polypropylene resins, polyvinyl chloride resins, polyvinylidene difluoride resins, polysulfone resins, polyethersulfone resins, polyacrylonitrile resins, polyolefin resins, cellulose resins and cellulose triacetate resins, and the material may be a mixture of resins containing these resins as major components. The major component means that the component is contained in an amount of not less than 50% by weight, preferably not less than 60% by weight. Among these, more preferred examples of the material of the porous membrane include those which can be easily formed by solutions and are excellent in physical durability and chemical resistance, such as polyvinyl chloride resins, polyvinylidene difluoride resins, polysulfone resins, polyethersulfone resins, polyacrylonitrile resins and polyolefin resins, among which polyvinylidene difluoride resins and resins containing these as major components are most preferably used.

As the polyvinylidene difluoride resin, a homopolymer of vinylidene fluoride is preferably used and, other than a homopolymer of vinylidene fluoride, a copolymer with vinyl monomers capable of copolymerizing with vinylidene fluoride is also preferably used. Examples of the vinyl monomers capable of copolymerizing with vinylidene fluoride include tetrafluoroethylene, hexafluoropropylene and ethylene fluoride trichloride.

Examples of the polyolefin resins include polyethylene, polypropylene, chlorinated polyethylene and chlorinated polypropylene, and chlorinated polyethylene is preferably used.

An overview of the preparation method of the porous membrane will now be described. First, on the surface of the above-mentioned porous base material, a coating of a starting solution containing the above-mentioned resin and a solvent is formed, while impregnating the starting solution into the porous base material. Thereafter, only the coated surface of the porous base material having the coating is brought into contact with a coagulation bath containing a nonsolvent to coagulate the resin, while forming a porous resin layer on the surface of the porous base material. The nonsolvent may also be further contained in the starting solution. The temperature of the starting solution is usually preferably selected within the range of 15 to 120° C. in view of the film-forming property.

To the starting solution, a pore-forming agent may be added. The pore-forming agent is extracted upon immersion in the coagulation bath, to make the resin layer porous. Addition of the pore-forming agent allows regulation of the average pore size. The pore-forming agent preferably has a high solubility in the coagulation bath. Examples of the pore-forming agent which may be used include inorganic salts such as calcium chloride and calcium carbonate. Further examples of the pore-forming agent which may be used include polyoxyalkylenes such as polyethylene glycol and polypropylene glycol; water-soluble macromolecular compounds such as polyvinyl alcohol, polyvinyl butyral and polyacrylic acid; and glycerin.

The solvent dissolves the resin. It acts on the resin and the pore-forming agent to promote formation of a porous resin layer by these. Examples of the solvent which may be used include N-methylpyrrolidinone (NMP), N,N-dimethylacetamide (DMAc), N,N-dimethylformamide (DMF), dimethylsulfoxide (DMSO), acetone and methyl ethyl ketone. Among these, NMP, DMAc, DMF and DMSO, in which resins show high solubilities, may be preferably used.

Further, a nonsolvent may also be added to the starting solution. A nonsolvent is a liquid which does not dissolve a resin. A nonsolvent has an action of regulating the rate of coagulation of a resin, to regulate the sizes of the pores. Examples of the nonsolvent which may be used include water and alcohols such as methanol and ethanol. Among these, water and methanol are preferred in view of the cost. The nonsolvent may also be a mixture of these.

As mentioned above, the porous membrane is preferably a porous membrane formed by a porous base material and a porous resin layer. The porous base material may be either impregnated with the porous resin layer or not impregnated with the porous resin layer, which is selected depending on the use. The average thickness of the porous base material is preferably selected within the range of 50 µm to 3000 µm. In cases where the porous membrane is a hollow fiber membrane, the inner diameter of the hollow fiber is preferably selected within the range of 200 µm to 5000 µm, and the membrane thickness is preferably selected within the range of 20 µm to 2000 µm. A fabric or a knit produced by forming an organic fiber or an inorganic fiber into a cylindrical shape may be contained in the hollow fiber.

The porous membrane may be made into a separation membrane element by combining it with a support. The form of the separation membrane element having a porous membrane is not restricted, and a separation membrane element wherein a supporting plate is used as the support and the porous membrane is placed on at least one side of the supporting plate is one preferred example of the separation membrane element having the porous membrane. In cases where it is difficult to secure a large membrane area in this example, placement of the porous membrane on the both sides of the supporting plate to increase the permeability is also a preferred example.

The average pore size of the porous membrane is not less than 0.01 µm and less than 1 µm. With an average pore size of the porous membrane within this range, a high blocking performance which does not allow leakage of cells and sludge and a high permeability can both be achieved and, further, clogging is less likely to occur, so that the permeability can be maintained with high accuracy and reproducibility for a long time. The average pore size of the porous membrane is preferably not more than 0.4 µm, and the operation can be more preferably carried out with an average pore size of less than 0.2 µm. In cases where the average pore size is too small, the permeability may decrease, so that the average pore size is not less than 0.01 µm, preferably not less than 0.02 µm, more preferably not less than 0.04 µm. The average pore size can be determined by measuring the diameters of all the pores which can be observed within an area of 9.2 µm×10.4 µm under the scanning electron microscope at a magnification of 10,000×, and averaging the measured values.

Further, the standard deviation σ of the average pore size is preferably not more than 0.1 µm. Further, in cases where the standard deviation of the average pore size is small, that is, in cases where the pore sizes are uniform, a uniform permeate is more likely to be obtained and hence simple management of the fermentation operation is possible, so that the standard deviation of the average pore size is preferably as small as possible.

The standard deviation σ of the average pore size is calculated according to (Equation 1) below wherein N represents the number of pores observable within the above-mentioned area of 9.2 µm×10.4 µm, Xk represents the respective measured diameters, and X(ave) represents the average of the pore sizes:

$$\sigma = \sqrt{\frac{\sum_{k=1}^{N}(X_k - X(ave))2}{N}}. \qquad \text{(Equation 1)}$$

In the porous membrane, the permeability to culture medium is one of its important properties. As an index of the permeability, the pure water permeability coefficient of the porous membrane before use can be employed. The pure water permeability coefficient of the porous membrane is preferably not less than $2\times10^{-9}$ m$^3$/m$^2$/s/pa when the amount of permeation is measured using purified water at a temperature of 25° C. prepared by filtration through a reverse osmosis membrane, with a head height of 1 m, and in cases where the pure water permeability coefficient is from $2\times10^{-9}$ m$^3$/m$^2$/s/pa to $6\times10^{-7}$ m$^3$/m$^2$/s/pa, an amount of permeation which is practically sufficient can be obtained.

The membrane surface roughness in the porous membrane is a factor that affects clogging of the separation membrane and, preferably, in cases where the membrane surface roughness is not more than 0.1 µm, the detachment coefficient and the membrane resistance of the separation membrane can be suitably suppressed. Hence, continuous fermentation can be carried out with a lower transmembrane pressure difference. Therefore, since clogging can be suppressed to allow stable continuous fermentation, the membrane surface roughness is preferably as small as possible.

Further, in cases where the membrane surface roughness is small, the shear force generated on the membrane surface during filtration of the microorganism can be expected to be small. Hence, destruction of the microorganism may be suppressed and clogging of the porous membrane may be suppressed. Therefore, it is thought that stable filtration is possible for a long time.

The membrane surface roughness can be measured using the following atomic force microscope (AFM) under the following conditions:
Device
Atomic force microscope (Nanoscope IIIa produced by Digital Instruments) Conditions
Probe: SiN cantilever (manufactured by Digital Instruments)
Scanning mode: Contact mode (measurement in air)
Underwater tapping mode (underwater measurement)
Scanning area: 10 µm×10 µm, 25 µm×25 µm (measurement in air)
5 µm×5 µm, 10 µm×10 µm (underwater measurement)
Scanning resolution: 512×512
Sample Preparation.
When the measurement was carried out, the membrane sample was soaked in ethanol at room temperature for 15 minutes and then soaked in RO water for 24 hours, followed by washing and drying it in the air.

The membrane surface roughness ($d_{rough}$) is calculated according to the following (Equation 2) using the above AFM, based on the heights of the respective points in the direction of the z-axis:

$$d_{rough} = \sum_{n=1}^{N} \frac{|Z_n - \bar{Z}|}{N} \qquad \text{(Equation 2)}$$

$d_{rough}$: Surface roughness (µm)
$Z_n$: Height in direction of z-axis (µm)
$\bar{Z}$: Average height (µm) in scanned area
N: Number of measured samples.

The transmembrane pressure difference during the filtration of a microorganism through a porous membrane in Step (A) may be one with which the membrane is not easily clogged with the microorganism and medium components, and it is important to carry out the filtration with a transmembrane pressure difference within the range of 0.1 to 20 kPa. The transmembrane pressure difference is preferably within the range of 0.1 to 10 kPa, more preferably within the range of 0.1 to 5 kPa, still more preferably within the range of 0.1 to 2 kPa. In cases where the transmembrane pressure difference is not within the above-described range, clogging with the microorganism and medium components may rapidly occur and the amount of permeation may decrease, causing a trouble during the operation of continuous fermentation.

In terms of the driving force of the filtration, a siphon using the liquid level difference (hydraulic head difference) between the fermentation culture medium and the permeate from the porous membrane may be used to generate the transmembrane pressure difference in the porous membrane. Further, as the driving force of the filtration, a suction pump may be placed in the permeate side of the porous membrane, or a pressure pump may be placed in the fermentation culture medium side of the porous membrane. The transmembrane pressure difference can be controlled by changing the liquid level difference between the fermentation culture medium and the permeate from the porous membrane. Further, in cases where a pump is used to generate the transmembrane pressure difference, the transmembrane pressure difference can be controlled by the suction pressure and, further, the transmembrane pressure difference can also be controlled by the pressure of the gas or liquid which is used for introducing the pressure from the fermentation culture medium side. In cases where such pressure control is carried out, the difference between the pressure in the fermentation culture medium side and the pressure in the permeate side of the porous membrane corresponds to the transmembrane pressure difference, and can be used for controlling the transmembrane pressure difference.

Figure 2:
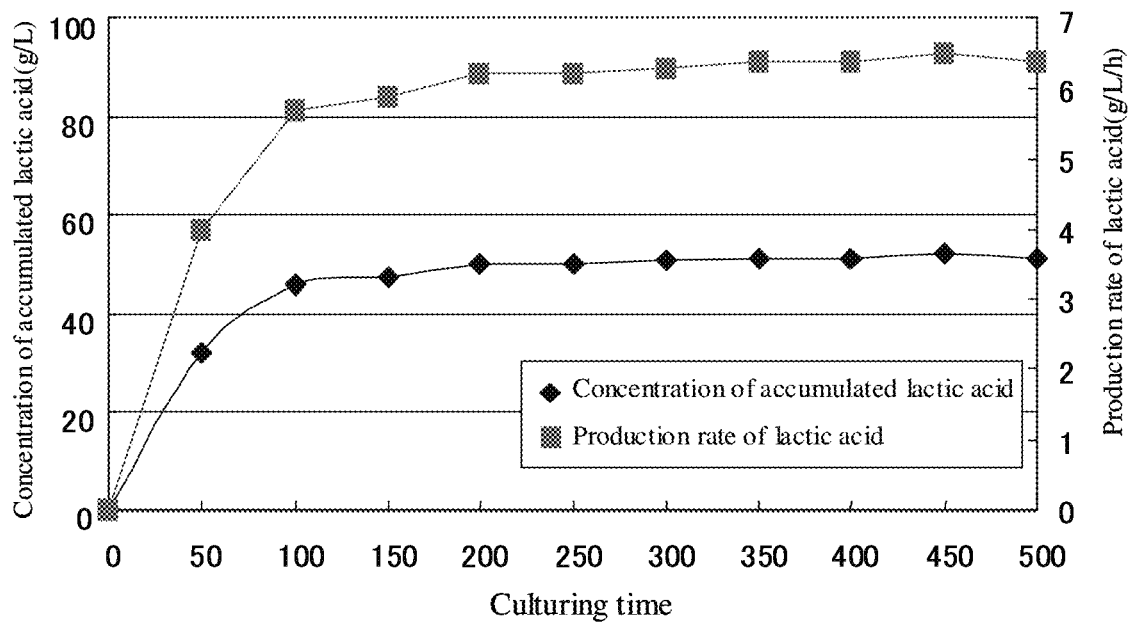
FIG. 2 is a diagram showing the concentration of lactic acid accumulated and the production rate of lactic acid during the continuous culture carried out in Example 1.

The continuous fermentation apparatus used in Step (A) is not restricted as long as the above conditions are satisfied, and preferred examples thereof include the ones disclosed in FIG. 1 and FIG. 2 in WO2007/097260. Further, the porous membrane element for filtration of a fermentation culture medium is not restricted as long as the above conditions are satisfied, and preferred examples thereof include the ones disclosed in FIG. 3 and FIG. 4 in WO2007/097260.

The fermentation feedstock is not restricted as long as it promotes the growth of the microorganism having an ability of lactic acid fermentation to be cultured, to allow satisfactory production of the lactic acid of interest. Preferred examples of the fermentation feedstock include conventional liquid media containing carbon sources, nitrogen sources, inorganic salts and, as appropriate, organic micronutrients such as amino acids and vitamins, when necessary. Examples of the carbon sources include sugars such as glucose, sucrose, fructose, galactose and lactose; saccharified starch solutions containing these sugars; sweet potato molasses; sugar beet molasses; high test molasses; and further, organic acids such as acetic acid; alcohols such as ethanol; and glycerin. Examples of the nitrogen sources include ammonia gas, aqueous ammonia, ammonium salts, urea and nitric acid salts; and other organic nitrogen sources used supplementarily such as oilcakes, soybean-hydrolyzed liquids, casein digests, other amino acids, vitamins, corn steep liquors, yeasts or yeast extracts, meat extracts, peptides such as peptones, and cells of various fermentation microorganisms and hydrolysates thereof. Examples of the inorganic salts which may be added as appropriate include phosphoric acid salts, magnesium salts, calcium salts, iron salts and manganese salts. In cases where the microorganism having an ability of lactic acid fermentation used requires particular nutrients for its growth, the nutrients may be added as preparations or natural products containing these. An anti-forming agent may also be added as required. The culture medium means a liquid obtained as a result of growth of a microorganism having an ability of lactic acid fermentation in a fermentation feedstock, and the composition of the fermentation feedstock to be further added may be changed as appropriate from the composition of the fermentation feedstock used at the beginning of the culture, such that the productivity of lactic acid is enhanced.

In the continuous culture operation in Step (A), Batch culture or Fed-Batch culture may be carried out at the initial phase of the culture to increase the microorganism concentration, followed by starting continuous culture (withdrawal), or the cells may be seeded at a high concentration and subjected to continuous culture from the beginning of the culture. It is possible to start supplying the feedstock medium and withdrawing the culture at appropriate timings. The timing of the start of supplying of the feedstock medium and the timing of the start of withdrawing of the culture are not necessarily the same. The supplying of the feedstock medium and the withdrawing of the culture may be carried out either continuously or intermittently. Nutrients as described above necessary for the growth of the cells may be added to the feedstock medium to allow continuous growth of the cells. The concentration of the microorganism in the culture medium is preferably maintained high within the range which does not cause death of the microorganism at a high rate due to an environment of the culture medium which is inappropriate for the growth of the microorganism, in view of achieving efficient production. For example, by maintaining the concentration at not less than 5 g/L in terms of dry weight, a good production efficiency can be obtained.

Further, as required, the microorganism may be removed from the fermenter. For example, since, in cases where the microorganism concentration in the fermenter is too high, clogging of the porous membrane is likely to occur, the removal may be carried out to avoid the clogging. Further, since the productive performance for lactic acid may change depending on the microorganism concentration in the fermenter, the removal of the microorganism may be carried out using the productive performance as an index, to maintain the productive performance.

The operation of continuous culture by allowing the growth of fresh cells having an ability of lactic acid fermentation is usually preferably carried out in a single fermenter in view of control of the culture. However, the number of the fermenter(s) is not restricted as long as the continuous culture is carried out to produce the product while allowing the growth of cells. A plurality of fermenters may be used because of, for example, a small capacity of each fermenter. In this case, a high productivity of the fermentation product can be obtained even by continuous culture using a plurality of fermenters connected in parallel or in series through pipes.

The filtration through a nanofiltration membrane in Step (B) will now be described.

The nanofiltration membrane is also called a nanofilter (nanofiltration membrane, NF membrane), and generally defined as "a membrane that allows permeation of monovalent ions, but blocks divalent ions." The membrane is considered to have fine voids having sizes of about several nanometers, and mainly used to block fine particles, molecules, ions and salts in water.

The term "filtration using a nanofiltration membrane" means that the permeate of Step (A) is filtered through a nanofiltration membrane to block or separate inorganic salts dissolved or deposited as solids, while allowing a lactic acid solution to permeate as a filtrate. The inorganic salts include any form of the inorganic salts contained in the culture medium, such as both those dissolved in the permeate of Step (A) and those deposited or precipitated in the permeate of Step (A).

In Step (B), it is preferred to adjust the pH of the permeate of Step (A) to not less than 2.0 and not more than 4.5. It is known that substances ionized in a solution are more likely to be removed or blocked by a nanofiltration membrane than non-ionized substances. Therefore, by adjusting the pH of the permeate of Step (A) to not more than 4.5, the ratio of lactic acid dissociated into lactate ions in the permeate becomes small, and this allows more efficient permeation of lactic acid. Further, in cases where the pH is less than 2.0, the nanofiltration may be damaged. Further, since pKa of lactic acid is 3.86, in cases where the pH is not more than 3.86, lactic acid that has not been dissociated into lactate ions and hydrogen ions is contained in the permeate of Step (A) in a larger amount, so that lactic acid can be efficiently allowed to permeate through the nanofiltration membrane, which is more preferred. The adjustment of the pH of the permeate of Step (A) may be carried out either when the microbial fermentation is carried out or after Step (A). Further, the pH may be adjusted by adding an inorganic or organic acid in cases where the pH of the permeate is to be made more acidic, or by adding an alkaline substance such as calcium hydroxide or aqueous ammonia in cases where the pH is to be made more alkaline.

The permeate of Step (A) to be applied to the nanofiltration membrane of Step (B) is preferably prepared by adding an alkaline substance to the culture medium of Step (A) to maintain an optimum pH for microbial fermentation and filtering the obtained culture medium through a porous membrane. The microorganism is usually cultured at a pH of 4 to 8, at a temperature of 20 to 40° C. The alkaline substance to be added is not restricted, and a basic calcium salt is preferably added.

In cases where Step (A) is a step of continuous fermentation in the presence of a calcium salt, Step (D), in which the calcium component in the permeate in Step (A) is removed as an insoluble sulfate, may be introduced before Step (B). More particularly, for example, Step (D) is carried out by adding sulfuric acid to the permeate of Step (A) and precipitating/filtering the calcium component in the permeate of Step (A) as calcium sulfate, which is an insoluble sulfate. By allowing the filtrate (separated liquid containing lactic acid) to pass through the nanofiltration membrane of Step (B), the calcium component can be more efficiently removed or blocked. Examples of the basic calcium salts include calcium hydroxide, calcium carbonate, calcium phosphate, calcium oxide and calcium acetate, and the basic calcium salt is preferably calcium hydroxide. In cases where the calcium component in the permeate of Step (A) is precipitated/filtered as an insoluble sulfate, if the number of equivalents of the sulfuric acid added to the culture medium exceeds the number of equivalents of the calcium (number of equivalents of sulfuric acid>number of equivalents of calcium), the excess sulfuric acid partially permeates through the nanofiltration membrane. If this is followed by exposure of the permeate of Step (B) to a condition under heat such as concentration or distillation, the permeated sulfuric acid may act as a catalyst for promotion of oligomerization of lactic acid, resulting in decrease in the distillation yield. Therefore, in cases where the calcium component in the permeate of Step (A) is precipitated/filtered as an insoluble sulfate, the number of equivalents of the sulfuric acid added is preferably not more than the number of equivalents of the calcium component in the permeate of Step (A). In cases where the number of equivalents of the sulfuric acid added is adjusted based on the pH, the pH is preferably not less than 2.0 since, in this case, the number of equivalents of the sulfuric acid is not more than the number of equivalents of the calcium component.

As a step preceding the above Step (D), Step (E), in which organic acids other than lactic acid are removed from the permeate of Step (A) while removing crystals of calcium lactate, may be introduced. More particularly, the pH is adjusted by addition of basic calcium to the permeate of Step (A), and the resulting permeate is filtered through a nanofiltration membrane equivalent to the one used in Step (B), thereby collecting an aqueous solution containing calcium lactate from the feed side and removing organic acids including acetic acid from the permeate side.

In Step (E), the pH of the permeate of Step (A) is preferably adjusted to not less than 6 and not more than 11. Since nanofiltration membranes have a property with which substances ionized (dissociated) in a solution are more likely to be blocked than non-ionized (undissociated) substances, by adjusting the pH of the culture medium to not less than 6, the ratio of lactic acid dissociated into ions in the culture medium (dissociated lactic acid/undissociated lactic acid) becomes higher than the ratio of acetic acid dissociated into ions (dissociated acetic acid/undissociated acetic acid). In this case, an aqueous solution containing calcium lactate can be efficiently collected from the feed side, and organic acids other than lactic acid can be efficiently separated from the permeate side. Further, in cases where the pH of the culture medium is higher than 11, durability of the nanofiltration membrane is adversely affected, which is not preferred.

In Step (E), the organic acids other than lactic acid separated from the permeate side of the nanofiltration membrane are those derived from the permeate of Step (A) or from the fermentation feedstock, and acetic acid is preferably separated.

Examples of the basic calcium preferably added in Step (E) to adjust the pH of the permeate of Step (A) include calcium hydroxide, calcium carbonate, calcium phosphate, calcium oxide and calcium acetate in the forms of solids and aqueous solutions, and the basic calcium is preferably calcium hydroxide. In cases where an aqueous solution is added, the concentration of the basic calcium is not restricted, and the basic calcium to be added may be in the form of a slurry having a concentration exceeding the saturation solubility.

Examples of the method for evaluating the extents of removal, blocking and filtration of inorganic salts dissolved or deposited as solids by the nanofiltration membrane include an evaluation method by calculating the removal rates (blocking rates) of inorganic ions, but the method is not restricted to this method. The blocking rate (removal rate) of an inorganic salt can be calculated according to Equation 3 by measuring the concentration of the inorganic salt contained in the raw liquid (culture medium) (raw liquid inorganic salt concentration) and the concentration of the inorganic salt contained in the permeate (lactic acid solution) (permeate inorganic salt concentration) by an analysis represented by ion chromatography.

Inorganic salt removal rate (%)=(1-(permeate inorganic salt concentration/raw liquid inorganic salt concentration))×100   (Equation 3)

The membrane separation performance of the nanofiltration membrane used in Step (B) is not restricted, and the ratio of the permeation rate of magnesium sulfate relative to the permeation rate of citric acid through the nanofiltration membrane is preferably not less than 3 at an operation pressure of 0.5 MPa, raw liquid temperature of 25° C. and concentration in the raw liquid of 1000 ppm. In cases where the ratio of the permeation rate of magnesium sulfate relative to the permeation rate of citric acid through the nanofiltration membrane under the above conditions is not less than 3, inorganic salts contained in the permeate of Step (A) can be removed and lactic acid can be allowed to permeate efficiently, which is preferred. The permeation rate of magnesium sulfate can be calculated according to Equation 4 by measuring the concentration of magnesium sulfate contained in the raw liquid (raw liquid magnesium sulfate concentration) and the concentration of magnesium sulfate contained in the permeate (permeate magnesium sulfate concentration) by an analysis represented by ion chromatography. Similarly, the permeation rate of citric acid can be calculated by replacing the magnesium sulfate concentration in Equation 4 with the citric acid concentration and measuring the concentration of citric acid contained in the raw liquid (raw liquid citric acid concentration) and the concentration of citric acid contained in the permeate (permeate citric acid concentration) by an analysis represented by high performance liquid chromatography.

Magnesium sulfate permeation rate (%)=(permeate magnesium sulfate concentration)/(raw liquid magnesium sulfate concentration)×100   (Equation 4)

Further, the permeation rate of magnesium sulfate is preferably not more than 1.5% at an operation pressure of 0.5 MPa, raw liquid temperature of 25° C. and concentration in the raw liquid of 1000 ppm. In cases where the permeation rate of magnesium sulfate through the nanofiltration membrane is higher than 1.5% under the above conditions, concentration of the lactic acid solution permeated through the nanofiltration membrane may cause deposition of inorganic salts, and a distillation operation is likely to cause racemization and oligomerization due to the influence of the permeated inorganic salts and may decrease the distillation yield. More preferably, the permeation rate of magnesium sulfate through the nanofiltration membrane is not more than 1.0%.

In addition, nanofiltration membranes having removal rates of sodium chloride (500 mg/L) of not less than 45% are preferably used. In terms of the permeation performance of the nanofiltration membrane, a nanofiltration membrane in which the permeation flow rate of sodium chloride (500 mg/L) per unit membrane area ($m^3/m^2/day$) at a filtration pressure of 0.3 MPa is not less than 0.5 and not more than 0.8 is preferably used. The permeation flow rate per unit membrane area (membrane permeation flux) can be evaluated by calculation according to Equation 5, by measuring the amount of the permeated liquid, collection time of the permeated liquid, and the membrane area.

$$\text{Membrane permeation flux } (m^3/m^2/day) = \text{amount of permeated liquid/membrane area/collection time} \quad \text{(Equation 5)}$$

Examples of the material of the nanofiltration membrane which may be used include macromolecular materials such as cellulose acetate polymers, polyamides, polyesters, polyimides and vinyl polymers. The membrane is not restricted to a membrane constituted by only one of the materials, and may be a membrane comprising plural membrane materials. In terms of the structure of the membrane, the membrane may be either an asymmetric membrane, which has a dense layer on at least one side of the membrane and micropores having pore sizes that gradually increase in the direction from the dense layer toward the inside of the membrane or the other side of the membrane, or a composite membrane, which has a very thin functional layer formed by another material on the dense layer of an asymmetric membrane. Examples of the composite membrane which may be used include the composite membrane described in JP 62-201606 A, which has a nanofilter composed of a polyamide functional layer on a support membrane comprising polysulfone as a membrane material.

Among these, a composite membrane having a functional layer composed of a polyamide is preferred since it has a high pressure resistance, high permeability and high solute-removal performance, which make the membrane highly potential. For maintenance of durability against operation pressure, high permeability and high blocking performance, a membrane having a structure in which a polyamide is used as a functional layer, which layer is retained by a support comprising a porous membrane and a non-woven fabric, is suitable. Further, as a polyamide semipermeable membrane, a composite nanofiltration membrane having, on a support, a functional layer of a cross-linked polyamide obtained by polycondensation reaction between a polyfunctional amine and a polyfunctional acid halide is suitable.

In the nanofiltration membrane having a functional layer composed of a polyamide, preferred examples of the carboxylic acid component of the monomers constituting the polyamide include aromatic carboxylic acids such as trimesic acid, benzophenone tetracarboxylic acid, trimellitic acid, pyromellitic acid, isophthalic acid, terephthalic acid, naphthalene dicarboxylic acid, diphenylcarboxylic acid and pyridinecarboxylic acid. In view of solubility to film-forming solvents, trimesic acid, isophthalic acid and terephthalic acid, and mixtures thereof are more preferred.

Preferred examples of the amine component of the monomers constituting the polyamide include primary diamines having an aromatic ring, such as m-phenylenediamine, p-phenylenediamine, benzidine, methylene bis dianiline, 4,4'-diaminobiphenylether, dianisidine, 3,3',4-triaminobiphenylether, 3,3',4,4'-tetraaminobiphenylether, 3,3'-dioxybenzidine, 1,8-naphthalenediamine, m(p)-monomethylphenylenediamine, 3,3'-monomethylamino-4,4'-diaminobiphenylether, 4,N,N'-(4-aminobenzoyl)-p(m)-phenylenediamine-2,2'-bis(4-aminophenylbenzoimidazole), 2,2'-bis(4-aminophenylbenzooxazole) and 2,2'-bis(4-aminophenylbenzothiazole); and secondary diamines such as piperazine, piperidine and derivatives thereof. Among these, a nanofiltration membrane having a functional layer composed of a cross-linked polyamide comprising piperazine or piperidine as monomers is preferably used since it has heat resistance and chemical resistance in addition to the pressure resistance and the durability. The polyamide more preferably contains as a major component the cross-linked piperazine polyamide or cross-linked piperidine polyamide and further contains a constituting component represented by Formula (1), still more preferably contains a cross-linked piperazine polyamide as a major component and further contains a constituting component represented by Formula (1). Further, preferably, in Formula (1), n=3. Examples of the nanofiltration membrane having a functional layer composed of a polyamide containing a cross-linked piperazine polyamide as a major component and further containing a constituting component represented by Formula (1) include the one described in JP 62-201606 A, and particular examples thereof include UTC60 manufactured by TORAY INDUSTRIES, INC., which is a cross-linked piperazine polyamide semipermeable membrane having a functional layer composed of a polyamide containing a cross-linked piperazine polyamide as a major component and further containing a constituting component represented by Formula (1), wherein n=3.

A nanofiltration membrane is generally used as a spiral-wound membrane element, and the nanofiltration membrane used is also preferably used as a spiral-wound membrane element. Particular preferred examples of the nanofiltration membrane element include GEsepa, which is a cellulose acetate nanofiltration membrane manufactured by GE Osmonics; NF99 and NF99HF, which are nanofiltration membranes having a functional layer composed of a polyamide, manufactured by Alfa-Laval; NF-45, NF-90, NF-200 and NF-400, which are nanofiltration membranes having a functional layer composed of a cross-linked piperazine polyamide, manufactured by Filmtec Corporation; and SU-210, SU-220, SU-600 and SU-610, which are nanofiltration membrane modules manufactured by TORAY INDUSTRIES, INC., having UTC60 manufactured by the same manufacturer, which has a functional layer composed of a polyamide containing a cross-linked piperazine polyamide as a major component and further containing a constituting component represented by Formula (1). The nanofiltration membrane element is more preferably NF99 or NF99HF, which are nanofiltration membranes having a functional layer composed of a polyamide, manufactured by Alfa-Laval; NF-45, NF-90, NF-200 or NF-400, which are nanofiltration membranes having a functional layer composed of a cross-linked piperazine polyamide, manufactured by Filmtec Corporation; or SU-210, SU-220, SU-600 or SU-610, which are nanofiltration membrane modules manufactured by TORAY INDUSTRIES, INC., having UTC60 manufactured by the same manufacturer, which has a functional layer composed of a polyamide containing a cross-linked piperazine polyamide as a major component and further containing a constituting component represented by Formula (1). The nanofiltration membrane element is still more preferably SU-210, SU-220, SU-600 or SU610, which are nanofiltration membrane modules manufactured by TORAY INDUSTRIES, INC., having UTC60 manufactured by the same manufacturer, which has a functional layer composed of a polyamide containing a cross-linked piperazine polyamide as a major component and further containing a constituting component represented by Formula (1).

The filtration through a nanofiltration membrane in the Step (B) may be carried out under pressure, and the filtration pressure is preferably within the range of 0.1 MPa to 8 MPa. In cases where the filtration pressure is less than 0.1 MPa, the membrane permeation rate may decrease, while in cases where the filtration pressure is more than 8 MPa, the membrane may be damaged. In cases where the membrane is used at a filtration pressure within the range of 0.5 MPa to 7 MPa, the membrane permeation flux is high, so that the lactic acid solution can be efficiently allowed to permeate and the possibility of damaging the membrane is small, which is more preferred. The membrane is especially preferably used at a filtration pressure within the range of 1 MPa to 6 MPa.

The concentration of lactic acid in Step (B) is not restricted, and in cases where the concentration is high, the concentration of lactic acid contained in the permeate of Step (B) is also high, so that the length of time required for the concentration can be shortened, which is preferred in view of cost reduction.

The concentrations of the inorganic salts in Step (B) are not restricted, and may be not less than the saturation solubility. That is, in cases where the concentration of an inorganic salt is not more than the saturation solubility, the inorganic salt is dissolved in the culture medium, and in cases where the concentration of the inorganic salt is not less than the saturation solubility, the inorganic salt is partially deposited. However, in Step (B), both inorganic salts dissolved in the permeate of Step (A) and inorganic salts deposited or precipitated in the permeate of Step (A) can be removed or blocked, so that lactic acid can be filtered without restriction by the concentrations of inorganic salts.

The permeability of lactic acid through the nanofiltration membrane upon separation of lactic acid contained in the permeate of Step (A) by the above method can be evaluated by calculating the lactic acid permeation rate. The lactic acid permeation rate can be calculated according to Equation 6 by measuring the concentration of lactic acid contained in the raw liquid (culture medium) (raw liquid lactic acid concentration) and the concentration of the lactic acid contained in the permeate (lactic acid-containing solution) (permeate lactic acid concentration) by an analysis represented by high performance liquid chromatography.

Lactic acid permeation rate (%)=(permeate lactic acid concentration/raw liquid lactic acid concentration)×100     (Equation 6)

In the method for producing lactic acid, the permeate of Step (B) is further subjected to distillation in Step (C), to obtain lactic acid with high purity. The distillation step is carried out under a reduced pressure of not less than 1 Pa and not more than atmospheric pressure (normal pressure, about 101 kPa). In cases where the step is carried out under a reduced pressure of not less than 10 Pa and not more than 30 kPa, the distillation temperature can be lower, which is more preferred. The distillation temperature in the cases where the step is carried out under reduced pressure is not less than 20° C. and not more than 200° C., but, in cases where the distillation is carried out at a temperature of not less than 180° C., racemization of lactic acid may be caused by the influence of impurities. Therefore, the distillation of lactic acid may be preferably carried out at a temperature of not less than 50° C. and not more than 180° C., more preferably not less than 60° C. and not more than 150° C.

Before subjecting to the Step (C), the permeate of Step (B) may once be concentrated using a concentrator such as an evaporator, or the permeate of Step (B) may be further subjected to Step (F), wherein the concentration of lactic acid is increased by filtration through a reverse osmosis membrane. In view of reducing energy for the concentration, Step (F) to increase the concentration of lactic acid by filtration through a reverse osmosis membrane is preferably employed.

The reverse osmosis membrane herein means a filter for removing ions and/or low molecular-weight molecules using as a driving force a pressure difference larger than the osmotic pressure of the liquid to be treated, and examples thereof which can be used include cellulose membranes such as those made of cellulose acetate and membranes prepared by polycondensing a polyfunctional amine compound and a polyfunctional acid halide to provide a separation functional layer made of a polyamide on a microporous support membrane. To suppress dirt, that is, fouling, on the surface of the reverse osmosis membrane, a low-fouling reverse osmosis membrane, which is mainly for sewage treatment, may also be preferably employed, which reverse osmosis membrane is prepared by covering the surface of a separation functional layer made of a polyamide with an aqueous solution of a compound having at least one reactive group reactive with an acid halide group, thereby allowing acid halide groups remaining on the surface the separation functional layer to form covalent bonds with the reactive groups. Since most of the divalent calcium ions have been removed in Step (B), stable membrane concentration can be carried out without formation of scale on the surface of the reverse osmosis membrane.

Examples of the reverse osmosis membrane preferably used include composite membranes having a cellulose acetate polymer as a functional layer (hereinafter referred to as cellulose acetate reverse osmosis membranes) and composite membranes having a polyamide functional layer (hereinafter referred to as polyamide reverse osmosis membranes). Examples of the cellulose acetate polymer include polymers prepared with organic acid esters of cellulose such as cellulose acetate, cellulose diacetate, cellulose triacetate, cellulose propionate and cellulose butyrate, which may be used solely, as a mixture, or as a mixed ester. Examples of the polyamide include linear polymers and cross-linked polymers constituted by aliphatic and/or aromatic diamine monomers.

Examples of the form of the membrane which may be used as appropriate include the flat membrane, spiral-wound membrane and hollow fiber membrane.

Particular examples of the reverse osmosis membrane include polyamide reverse osmosis membrane modules manufactured by TORAY INDUSTRIES, INC., such as low-pressure type modules SU-710, SU-720, SU-720F, SU-710L, SU-720L, SU-720LF, SU-720R, SU-710P and SU-720P, as well as high-pressure type modules SU-810, SU-820, SU-820L and SU-820FA containing UTC70 as the reverse osmosis membrane; cellulose acetate reverse osmosis membranes manufactured by the same manufacturer SC-L100R, SC-L200R, SC-1100, SC-1200, SC-2100, SC-2200, SC-3100, SC-3200, SC-8100 and SC-8200; NTR-759HR, NTR-729HF, NTR-70SWC, ES10-D, ES20-D, ES20-U, ES15-D, ES15-U and LF10-D manufactured by Nitto Denko Corporation; RO98pHt, R099, HR98PP and CE4040C-30D manufactured by Alfa-Laval; GE Sepa manufactured by GE; and BW30-4040, TW30-4040, XLE-4040, LP-4040, LE-4040, SW30-4040 and SW30HRLE-4040 manufactured by FilmTec Corporation.

Lactic Acid

We discovered that the lactic acid obtained by the above method for producing lactic acid contains only small amounts of impurities and, hence, the quality of the lactic acid is high enough to be used for production of a polylactic acid by direct polymerization. Further, we specified the ranges of the contents of impurities with which high-quality lactide (raw material for polylactic acid) and polylactic acid can be obtained. The first feature of the lactic acid is that the lactic acid contains, as an impurity in 90% aqueous lactic acid solution, methanol at a concentration of not more than 70 ppm, preferably not more than 65 ppm, more preferably not more than 50 ppm, still more preferably not more than 30 ppm. The content of methanol in 90% aqueous lactic acid solution can be measured by gas chromatography (GC). In cases where the lactic acid has a content, in 90% aqueous lactic acid solution, of methanol of more than 70 ppm, the polylactic acid obtained by direct dehydration polycondensation of the lactic acid has a low weight average molecular weight and a low mechanical strength, which is not preferred. Further, in cases where lactic acid having a content of methanol of more than 70 ppm was used, the synthetic yield of lactide decreases, which is not preferred.

The second feature of the lactic acid is that the lactic acid contains, as an impurity in 90% aqueous lactic acid solution, pyruvic acid at a concentration of not more than 500 ppm, preferably not more than 400 ppm, more preferably not more than 300 ppm. The content of pyruvic acid in 90% aqueous lactic acid solution can be measured by high performance liquid chromatography (HPLC). In cases where the lactic acid has a content, in 90% aqueous lactic acid solution, of pyruvic acid of more than 500 ppm, undesirable hue is obtained for polylactic acid produced by polymerization of the lactic acid. The hue of a polylactic acid can be evaluated based on the degree of coloration and, as an index of the degree of coloration, the APHA unit color number may be used. The American Public Health Association (APHA) unit color number (Hazen color number) is a value calculated according to the measurement method of JISK0071-1 (established on Oct. 20, 1998). Further, in cases where lactic acid having a content of pyruvic acid of more than 500 ppm was used, the synthetic yield of lactide decreases and the APHA unit color number increases, which are not preferred.

The third feature of the lactic acid is that the lactic acid contains, as an impurity in 90% aqueous lactic acid solution, furfural at a concentration of not more than 15 ppm, preferably not more than 10 ppm, more preferably not more than 5 ppm. The content of furfural in 90% aqueous lactic acid solution can be measured by high performance liquid chromatography (HPLC). In cases where the lactic acid has a content, in 90% aqueous lactic acid solution, of furfural of more than 10 ppm, undesirable hue and thermal stability are obtained for polylactic acid produced by polymerization of the lactic acid. The thermal stability of a polylactic acid can be evaluated based on the thermal weight loss rate. Further, in cases where lactic acid having a content of furfural of more than 15 ppm was used, increase in the APHA unit color number occurs in the obtained lactide, which is not preferred.

The fourth feature of the lactic acid is that the lactic acid contains, as an impurity in 90% aqueous lactic acid solution, 5-hydroxymethylfurfural at a concentration of not more than 15 ppm, preferably not more than 10 ppm, more preferably not more than 5 ppm. The content of 5-hydroxymethylfurfural in 90% aqueous lactic acid solution can be measured by high performance liquid chromatography (HPLC). Polylactic acid obtained by polymerization of lactic acid having a content, in 90% aqueous lactic acid solution, of 5-hydroxymethylfurfural of more than 10 ppm has undesirable hue and thermal stability. Further, in cases where lactic acid having a content of 5-hydroxymethylfurfural of more than 15 ppm was used, increase in the APHA unit color number occurs in the obtained lactide, which is not preferred.

The fifth feature of the lactic acid is that the lactic acid contains, as an impurity in 90% aqueous lactic acid solution, methyl lactate at a concentration of not more than 600 ppm, preferably not more than 400 ppm, more preferably not more than 100 ppm. The content of methyl lactate in 90% aqueous lactic acid solution can be measured by gas chromatography (GC). In cases where the lactic acid has a content, in 90% aqueous lactic acid solution, of methyl lactate of more than 600 ppm, the polylactic acid obtained by direct dehydration polycondensation of the lactic acid has a low weight average molecular weight and a low mechanical strength, which is not preferred. Further, in cases where lactic acid having a content of methyl lactate of more than 600 ppm was used, increase in the APHA unit color number occurs in the obtained lactide, which is not preferred.

The sixth feature of the lactic acid is that the lactic acid contains, as an impurity in 90% aqueous lactic acid solution, acetic acid at a concentration of not more than 500 ppm, preferably not more than 400 ppm, more preferably not more than 300 ppm. The content of acetic acid in 90% aqueous lactic acid solution can be measured by high performance liquid chromatography (HPLC). Polylactic acid obtained by polymerization of lactic acid having a content, in 90% aqueous lactic acid solution, of acetic acid of more than 500 ppm has undesirable thermal stability. Further, in cases where lactic acid having a content of acetic acid of more than 500 ppm was used, the synthetic yield of lactide decreases, which is not preferred.

The seventh feature of the lactic acid is that the lactic acid contains, as an impurity in 90% aqueous lactic acid solution, 2-hydroxybutyric acid at a concentration of not more than 500 ppm, preferably not more than 300 ppm, more preferably not more than 200 ppm. The content of 2-hydroxybutyric acid in 90% aqueous lactic acid solution can be measured by high performance liquid chromatography (HPLC). Polylactic acid obtained by polymerization of lactic acid having a content, in 90% aqueous lactic acid solution, of 2-hydroxybutyric acid of more than 500 ppm has undesirable thermal stability. Further, in cases where lactic acid having a content of 2-hydroxybutyric acid of more than 500 ppm was used, the synthetic yield of lactide decreases, which is not preferred.

The lactic acid may be either one of the (L)-body or the (D)-body, or a mixture of the (L)-body and the (D)-body. In cases where the lactic acid is a mixture, the optical purity, which indicates the isomer content of the (L)-body or the (D)-body, is preferably not less than 90% since the melting point of the obtained polylactic acid is high in this case. The optical purity is more preferably not less than 95%, still more preferably not less than 99%, most preferably not less than 99.9%.

A lactide produced by using the lactic acid as a raw material and the method for producing the lactide; and a polylactic acid produced by using the lactic acid as a raw material and the method for producing the polylactic acid; are also included in this disclosure.

Lactide

The lactide includes L,L-lactide, D,D-lactide and D,L-lactide, which are composed of L-lactic acid and/or D-lactic acid. The lactide is preferably L,L-lactide or D,D-lactide.

The method for producing the lactide is not restricted, and a conventional method, in which lactic acid is heated under reduced pressure to produce lactic acid oligomers, which are then depolymerized by heating in the presence of a catalyst under reduced pressure, to cause conversion into lactide, may be preferably used. The catalyst used for the depolymerization of lactic acid oligomers is not restricted, and is usually a catalyst having a metal selected from the group consisting of Group IA, Group IIIA, Group IVA, Group IIB, Group IVB and Group VA in the periodic table, or having a metal compound containing it.

Examples of the catalyst having a metal belonging to Group IA include hydroxides of alkali metals (e.g., sodium hydroxide, potassium hydroxide and lithium hydroxide), salts between alkali metals and weak acids (e.g., sodium lactate, sodium acetate, sodium carbonate, sodium octylate, sodium stearate, potassium lactate, potassium acetate, potassium carbonate and potassium octylate), and alkoxides of alkali metals (e.g., sodium methoxide, potassium methoxide, sodium ethoxide and potassium ethoxide).

Examples of the catalyst having a metal belonging to Group IIIA include aluminum ethoxide, aluminum isopropoxide, aluminum oxide and aluminum chloride.

Examples of the catalyst having a metal belonging to Group IVA include organotin catalysts (tin lactate, tin tartrate, tin dicaprylate, tin dilaurate, tin dipalmitate, tin distearate, tin dioleate, tin α-naphthoate, tin β-naphthoate and tin octylate) as well as tin powder, tin oxide and tin halides.

Examples of the catalyst having a metal belonging to Group IIB include zinc powder, zinc halides, zinc oxide, and organozinc compounds.

Examples of the catalyst having a metal belonging to Group IVB include titanium compounds such as tetrapropyl titanate; and zirconium compounds such as zirconium isopropoxide.

Examples of the catalyst having a metal belonging to Group VA include antimony compounds such as antimony trioxide; and bismuth compounds such as bismuth(III) oxide.

Among these, a catalyst having tin or a tin compound is preferred in view of the activity, and tin octylate is especially preferred.

The amount of the catalyst to be used is about 0.01 to 20% by weight, preferably about 0.05 to 15% by weight, more preferably about 0.1 to 10% by weight, with respect to the lactic acid oligomers.

The depolymerization reaction may be carried out using a conventional vertical reaction vessel, or may be carried out using a molecular still. Examples of the molecular still include those of the pot still type, the falling film type and the centrifugal type. The falling film type and centrifugal type apparatuses are continuous process apparatuses, and industrially widely used. A centrifugal type molecular still employs a method in which a film of a vaporized substance is expanded on a heated surface using the centrifugal force, and a falling film type molecular still employs a method in which a vaporized substance is allowed to flow down along a heated surface to form a thin film of the vaporized substance.

The depolymerization temperature is set to 160 to 300° C., preferably 180 to 260° C., more preferably 190 to 250° C. In cases where the temperature is lower than 160° C., distillation of lactide is difficult, and a considerably high degree of vacuum is required. On the other hand, in cases where the temperature is higher than 300° C., racemization and coloration are likely to occur.

The pressure inside the depolymerization apparatus is not more than the vapor pressure of lactide at the depolymerization temperature, and usually about 1 to 50 Torr. A lower pressure is preferred since, in this case, the heating temperature may be low. More particularly, the pressure is preferably 1 to 20 Torr, more preferably 1 to 10 Torr, still more preferably 1 to 5 Torr.

The residence time in the depolymerization apparatus is preferably as short as possible in view of preventing racemization, and usually not more than 1 hour. Use of a molecular still is preferred since, in this case, the time may be not more than 10 minutes, preferably not more than 3 minutes, more preferably not more than 1 minute.

The lactide produced by the method for producing lactide can be removed to the outside of the depolymerization reaction system as a vapor, and collected. The collection of lactide can be simply carried out using a condenser attached to the depolymerization apparatus.

Polylactic Acid

The polylactic acid includes a homopolymer of L-lactic acid units or D-lactic acid units; a polylactic acid block copolymer constituted by a segment composed of poly-L-lactic acid units and a segment composed of poly-D-lactic acid units; and a copolymer with monomers other than lactic acid. In cases where the polylactic acid is a copolymer, examples of the monomer units other than lactic acid include glycol compounds such as ethylene glycol, propylene glycol, butanediol, heptanediol, hexanediol, octanediol, nonanediol, decanediol, 1,4-cyclohexanedimethanol, neopentyl glycol, glycerin, pentaerythritol, bisphenol A, polyethylene glycol, polypropylene glycol and polytetramethylene glycol; dicarboxylic acids such as oxalic acid, adipic acid, sebacic acid, azelaic acid, dodecanedioic acid, malonic acid, glutaric acid, cyclohexanedicarboxylic acid, terephthalic acid, isophthalic acid, phthalic acid, naphthalenedicarboxylic acid, bis(p-carboxyphenyl)methane, anthracenedicarboxylic acid, diphenyl ether dicarboxylic acid, sodium sulfoisophthalic acid and tetrabutyl phosphonium isophthalic acid; hydroxycarboxylic acids such as glycolic acid, hydroxypropionic acid, hydroxybutyric acid, hydroxyvaleric acid, hydroxycaproic acid and hydroxybenzoic acid; and lactones such as caprolactone, valerolactone, propiolactone, undecalactone and 1,5-oxepan-2-one. The amount of copolymerization of the above-described other copolymerization components is preferably 0 to 30 mol %, more preferably 0 to 10 mol % with respect to the total monomer components.

The method for producing the polylactic acid is not restricted, and a conventional production method for polylactic acid may be used. Particular examples of the known method include the lactide method constituted by two steps, wherein lactide, which is a cyclic dimer, is first produced using lactic acid as a raw material, followed by performing ring-opening polymerization; and the direct polymerization method constituted by a single step, wherein the raw material is subjected to direct dehydration polycondensation in a solvent. Any of these methods may be used.

In the lactide method and the direct polymerization method, the length of time required for the polymerization can be shortened by using a catalyst for the polymerization reaction. Examples of the catalyst include metals such as tin, zinc, lead, titanium, bismuth, zirconium, germanium, antimony and aluminum, and derivatives thereof. The derivatives are preferably metal alkoxides, carboxylates, carbonates, oxides and halides. Particular examples thereof include tin chloride, tin acetate, tin octylate, zinc chloride, lead oxide, lead carbonate, titanium chloride, alkoxytitanium, germanium oxide and zirconium oxide. Among these, tin compounds are preferred, and tin acetate and tin octylate are more preferred.

The polymerization reaction may be carried out in the presence of the above catalyst usually at a temperature of 100 to 200° C., although the temperature varies depending on the type of the catalyst. Further, to remove water produced by the polymerization reaction, the polymerization reaction is preferably carried out under reduced pressure, and the pressure is preferably not more than 7 kPa, more preferably not more than 1.5 kPa.

For the polymerization reaction, a compound having two or more hydroxyl groups or amino groups in the molecule may be used as a polymerization initiator. Examples of the compound to be used as a polymerization initiator, which has two or more hydroxyl groups or amino groups in the molecule, include polyols such as ethylene glycol, propylene glycol, butanediol, hexanediol, octanediol, neopentyl glycol, diethylene glycol, triethylene glycol, polyethylene glycol, polypropylene glycol, glycerin, trimethylolpropane, pentaerythritol, dipentaerythritol, tripentaerythritol, sorbitol, poly(vinyl alcohol), poly(hydroxyethyl methacrylate) and poly(hydroxypropyl methacrylate); and polyvalent amines such as ethylenediamine, propylenediamine, butanediamine, hexanediamine, diethylenetriamine and melamine; among which polyols are more preferred.

The amount of the polymerization initiator to be added is not restricted, and preferably 0.001 to 5 parts by weight, more preferably 0.01 to 3 parts by weight with respect to 100 parts by weight of the raw material used (L-lactic acid, D-lactic acid, L,L-lactide or D,D-lactide).

In cases where the polylactic acid is produced by the direct polymerization method, the lactic acid used as a raw material needs to be highly pure, and the lactic acid can be sufficiently applied to the direct polymerization method. The solvent used for the direct polymerization method is not restricted as long as it does not adversely affect the polymerization, and may be water or an organic solvent. Examples of the organic solvent include aromatic hydrocarbons. Examples of the aromatic hydrocarbons include toluene, xylene, naphthalene, chlorobenzene and diphenyl ether. In cases where the polylactic acid is produced by the direct polymerization method, by removing water produced by the condensation reaction to the outside of the system, the polymerization can be promoted. The method of removal to the outside of the system is preferably polymerization under reduced pressure, and the pressure is preferably not more than 7 kPa, more preferably not more than 1.5 kPa.

The polylactic acid characteristically has a weight average molecular weight of not less than 120000, a thermal weight loss rate of less than 6.5% under a nitrogen atmosphere at a constant temperature of 200° C. with a heating time of 20 minutes, and an APHA unit color number of not more than 15. In cases where the weight average molecular weight of the polylactic acid is not less than 120000, preferably not less than 140000, the polylactic acid has an excellent mechanical strength; in cases where the thermal weight loss rate is less than 6.5%, preferably not more than 6.0%, the polylactic acid has an excellent thermal stability; and in cases where APHA is not more than 15, preferably not more than 10, the polylactic acid has an excellent hue; so that the polylactic acid that satisfies these physical properties is suitable for various uses such as fibers, films and molded articles.

EXAMPLES

Our methods will now be described in more detail, but the disclosure is not restricted to the Examples below.

As a microorganism having an ability of L-lactic acid fermentation, *Saccharomyces cerevisiae* to which an L-lactate dehydrogenase gene (L-LDH gene) derived from *Xenopus laevis* having the base sequence shown in SEQ ID NO:1 was introduced to the chromosome was used.

(Reference Example 1) Preparation of Yeast Strain Having Ability of L-Lactic Acid Fermentation A strain bred from the B3 strain described in JP 2008-029329 A was used as a yeast strain having an ability of L-lactic acid fermentation. The method of breeding is described below.

To the B3 strain, the L-LDH gene shown in SEQ ID NO:1 was introduced at the SED1 locus. For the introduction to the SED1 locus, PCR was carried out using pTRS102 described in JP 2008-029329 A as an amplification template, and oligonucleotides (SEQ ID NOs:2 and 3) as a primer set, to amplify a PCR fragment of 1.3 kb containing the L-LDH gene derived from *Xenopus laevis* and the TDH3 terminator sequence. SEQ ID NO:2 was designed such that the sequence corresponding to the sequence of 60 bp in the upstream of the initiation codon of the SED1 gene was added.

Subsequently, by PCR using the plasmid pRS423 as an amplification template, and oligonucleotides (SEQ ID NOs:4 and 5) as a primer set, a PCR fragment of about 1.3 kb containing the HIS3 gene, which is a yeast selection marker, was amplified. SEQ ID NO:5 was designed such that the sequence corresponding to the sequence of 60 bp in the downstream of the stop codon of the SED1 gene was added.

Each DNA fragment was separated by 1% agarose gel electrophoresis and purified according to a conventional method. PCR was carried out using a mixture of the obtained two types of fragments of about 1.3 kb as an amplification template, and oligonucleotides (SEQ ID NOs:2 and 5) as a primer set, to amplify a PCR fragment of about 2.6 kb in which the L-LDH gene derived from *Xenopus laevis*, the TDH3 terminator and the HIS3 gene are linked together and the sequences corresponding to the sequences of 60 bp in the upstream/downstream of the SED1 gene were added to the 5'-end and 3'-end, respectively.

The above DNA fragment was separated by 1% agarose gel electrophoresis and purified according to a conventional method. The B3 strain was transformed with the DNA fragment and cultured in a histidine-free medium, to select a transformant in which the L-LDH gene derived from *Xenopus laevis* was introduced to the downstream of the SED1 gene promoter in the chromosome.

Confirmation of the fact that the thus obtained transformant is yeast having the L-LDH gene derived from *Xenopus laevis* introduced to the downstream of the SED1 gene promoter in the chromosome was carried out as follows. The genomic DNA of the transformant was prepared using the genomic DNA extraction kit Dr. GenTLE (manufactured by TAKARA BIO INC.), and PCR was then carried out using the prepared genomic DNA as an amplification template, and oligonucleotides (SEQ ID NOs:6 and 7) as a primer set, to confirm whether an amplified DNA fragment of about 2.9 kb was obtained. In the non-transformed strain, an amplified DNA fragment of about 1.4 kb is obtained by the above PCR. The transformant having the L-LDH gene derived from *Xenopus laevis* introduced to the downstream of the SED1 gene promoter in the chromosome is hereinafter referred to as the B4 strain.

Subsequently, the yeast SW015 strain described in JP 2008-48726 A, having a temperature-sensitive mutation in the pdc5 gene, was mated with the B4 strain obtained as described above, to obtain diploid cells. The diploid cells were cultured in an ascus formation medium to allow ascus formation. Asci were dissected using a micromanipulator to obtain the respective haploid cells, which were then studied for auxotrophy. Among the obtained haploid cells, a strain having the L-LDH gene derived from *Xenopus laevis*, which is inserted in the PDC1, SED1 and TDH3 loci, and the temperature-sensitive mutation in the PDC5 gene (nonviable at 34° C.) was obtained, and the respective mating types MATa and MATα were selected. Among the obtained yeast strains, the one having the mating type of MATa was designated the SU014-8A strain, and the one having the mating type of MATα was designated the SU014-3B strain.

Subsequently, the lysine auxotrophy of the SU014-8A strain was restored. Using the genomic DNA of BY4741 manufactured by Funakoshi Corporation as a template, and oligonucleotides (SEQ ID NOs:8 and 9) as a primer set, PCR was carried out to amplify a PCR fragment of about 2 kb corresponding to the first half of the LYS2 gene. The above PCR fragment was separated by 1% agarose gel electrophoresis and purified according to a conventional method. The SU014-8A strain was transformed with the PCR fragment, to cancel the amber mutation of the LYS2 gene. By culturing the resultant in a lysine-free medium, a transformant having a restored lysine synthetic capacity was selected.

Confirmation of the fact that the thus obtained transformant is yeast in which the amber mutation of the LYS2 gene was canceled was carried out as follows. First, the obtained transformant was mated with the 20GY77 strain having the wild-type LYS2 gene, to obtain diploid cells. The diploid cells were cultured in an ascus formation medium to allow ascus formation. Asci were dissected using a micromanipulator to obtain the respective haploid cells, which were then studied for auxotrophy. It was confirmed that all the obtained haploid cells have the lysine synthetic capacity. In cases where the lysine synthetic capacity was restored without cancellation of the mutation of LYS2, cells which do not have the lysine synthetic capacity are obtained among the haploid cells obtained as described above. The strain obtained by the restoration of the lysine synthetic capacity of the SU014-8A strain is hereinafter referred to as HI001.

Subsequently, the leucine auxotrophy of the SU014-3B strain was restored. Using pRS425 as a template, and oligonucleotides (SEQ ID NOs:10 and 11) as a primer set, PCR was carried out to amplify a PCR fragment of the LEU2 gene of about 2 kb. The above PCR fragment was separated by 1% agarose gel electrophoresis and purified according to a conventional method. The SU014-3B strain was transformed with the PCR fragment, to cancel the mutation of the LEU2 gene. By culturing the resultant in a leucine-free medium, a transformant having a restored leucine synthetic capacity was selected.

Confirmation of the fact that the thus obtained transformant is yeast in which the mutation of the LEU2 gene was canceled was carried out as follows. First, the obtained transformant was mated with the 20GY7 strain having the wild-type LEU2 gene, to obtain diploid cells. The diploid cells were cultured in an ascus formation medium to allow ascus formation. Asci were dissected using a micromanipulator to obtain the respective haploid cells, which were then studied for auxotrophy. It was confirmed that all the obtained haploid cells have the leucine synthetic capacity. In cases where the leucine synthetic capacity was restored without cancellation of the mutation of the LEU2 gene, cells which do not have the leucine synthetic capacity are obtained among the haploid cells obtained as described above. The strain obtained by the restoration of the leucine synthetic capacity of the SU014-3B strain is hereinafter referred to as HI002.

Subsequently, the thus obtained HI001 strain and HI002 strain were mated with each other to obtain a diploid prototrophic strain, which does not have auxotrophy. The obtained strain is hereinafter referred to as the HI003 strain.

Lactic acid was confirmed by measuring the amount of lactic acid by HPLC under the following conditions:

Column: Shim-Pack SPR-H (manufactured by Shimadzu Corporation)

Mobile phase: 5 mM p-toluenesulfonic acid (flow rate: 0.8 mL/min.)

Reaction solution: 5 mM p-toluenesulfonic acid, 20 mM Bis-Tris, 0.1 mM EDTA

2Na (flow rate: 0.8 mL/min.)

Detection method: electric conductivity

Temperature: 45° C.

Measurement of the optical purity of L-lactic acid or D-lactic acid was carried out by HPLC under the following conditions:

Column: TSK-gel Enantio L1 (manufactured by Tosoh Corporation)

Mobile phase: 1 mM aqueous copper sulfate solution

Flow rate: 1.0 ml/min.

Detection method: UV 254 nm

Temperature: 30° C.

The optical purity of lactic acid was calculated by the following equation:

$$\text{Optical purity (\%)} = 100 \times (L-D) \text{ or } (D-L)/(L+D)$$

wherein L represents the concentration of L-lactic acid, and D represents the concentration of D-lactic acid.

(Reference Example 2) Production of L-Lactic Acid by Batch Fermentation

Using the HI003 strain prepared in Reference Example 1 and a raw material sugar medium (70 g/L Yutosei (manufactured by MUSO Co., Ltd.)), a batch fermentation test was carried out. The medium was autoclaved (121° C., 15 minutes) before use. Evaluation of the concentration of lactic acid, which is the product, was carried out using HPLC shown in Reference Example 1, and the glucose concentration was measured using Glucose Test Wako C (manufactured by Wako Pure Chemical Industries, Ltd.). The operating conditions of the batch fermentation apparatus of Reference Example 2 were as shown below:

Fermenter capacity (amount of lactic acid fermentation medium), 2 (L); temperature adjustment, 32 (° C.); ventilation volume for fermenter, 0.1 (L/min.); stirring rate of fermenter, 200 (rpm); pH adjustment, adjusted to pH 5 with 1 N calcium hydroxide.

First, the HI003 strain was cultured in 5 ml of the raw material sugar medium in a test tube overnight with shaking (pre-preculture). The pre-preculture medium was inoculated to 100 ml of a fresh raw material sugar medium and subjected to culture in a 500 ml Sakaguchi flask for 24 hours with shaking (preculture). Temperature adjustment and pH adjustment were carried out, and fermentation culture was performed. As a result of the batch fermentation for 50 hours, the concentration of accumulated lactic acid was 45 to 49 g/L, and the optical purity was 99.9% for L-lactic acid.

(Reference Example 3) Continuous Fermentation Process

Using the HI003 strain prepared in Reference Example 1, continuous fermentation of lactic acid was carried out with the culture apparatus shown in FIG. 1. Removal of the permeate from the membrane separation vessel was carried out using a Masterflex pump. As a medium, a raw material sugar medium (70 g/L Yutosei (manufactured by MUSO Co., Ltd.), 1.5 g/L ammonium sulfate) was used. This raw material sugar medium was autoclaved at a temperature of 121° C. for 15 minutes at a high pressure (2 atm) before use. As a porous membrane element member, a molded article made of stainless steel and a polysulfone resin was used, and, as a porous membrane, a hollow fiber membrane prepared by the method described in Reference Example 13 of WO2007/097260 was used. The operating conditions were as follows:
  Capacity of culture reactor: 20 (L)
  Volume of culture medium in culture reactor: 15 (L)
  Porous membrane used: PVDF filtration membrane
  Effective filtration area of membrane separation element: 2800 cm$^2$
  Temperature adjustment: 32 (° C.)
  Ventilation volume for culture reactor: air, 1 (L/min.)
  Stirring rate of culture reactor: 800 (rpm)
  pH adjustment: adjusted to pH 5 with 5 N calcium hydroxide
  Sterilization: 121° C., 0.2 MPa, 20 min., for all of the culture reactor including porous membrane element, and medium used
  Removal rate of culture medium: 0.16 m$^3$/m$^2$/d.

Removal of culture medium by a Masterflex pump was started 50 hours after the initiation of the culture, and the culture was continued until 500 hours after the initiation of the culture. The results of measurement of the concentration of lactic acid, which is the product, and the lactic acid production rate are shown in FIG. 2. The lactic acid concentration was measured by the method shown in Reference Example 1, and the lactic acid production rate was calculated using the Equation 7 below:

Lactic acid production rate (g/L/hr)=concentration of lactic acid accumulated in removed liquid (g/L)×removal rate of fermentation liquid (L/hr)/operational liquid volume of apparatus (L)   (Equation 7).

As a result, the transmembrane pressure difference did not exceed 1 kPa and stable operation was possible, without causing clogging of the membrane. The average lactic acid production rate during the period from 50 hours to 500 hours after the initiation of the culture was 6 g/L/h. Lactic acid obtained from the permeate of the porous membrane during the period from 400 hours to 500 hours after the initiation of the culture was used in the subsequent Examples (lactic acid concentration: 52 g/L, L-lactic acid optical purity: 99.9%).

(Reference Example 4) Evaluation of Permeability of Magnesium Sulfate Through Nanofiltration Membrane To 10 L of ultrapure water, 10 g of magnesium sulfate (manufactured by Wako Pure Chemical Industries, Ltd.) was added, and the resulting mixture was stirred at 25° C. for 1 hour, to prepare 1000 ppm aqueous magnesium sulfate solution. Subsequently 10 L of the prepared aqueous magnesium sulfate solution was fed to the raw liquid tank 13 of the membrane filtration apparatus shown in FIG. 3. As the 90φ nanofiltration membrane indicated by the symbol 19 in FIG. 4, a cross-linked piperazine polyamide nanofiltration membrane "UTC60" (nanofiltration membrane 1, manufactured by TORAY INDUSTRIES, INC.), a cross-linked piperazine polyamide nanofiltration membrane "NF-400" (nanofiltration membrane 2, manufactured by Filmtec Corporation), a polyamide nanofiltration membrane "NF99" (nanofiltration membrane 3, manufactured by Alfa-Laval) or a cellulose acetate nanofiltration membrane "GEsepa" (nanofiltration membrane 4, manufactured by GE Osmonics) was placed in a cell made of stainless steel (SUS316). The raw liquid temperature was adjusted to 25° C., and the pressure of the high-pressure pump 15 was adjusted to 0.5 MPa, to collect the permeate 16. The concentrations of magnesium sulfate contained in the raw liquid tank 13 and the permeate 16 were analyzed by ion chromatography (manufactured by Dionex Corporation) under the following conditions, thereby calculating the permeation rate of magnesium sulfate.

Anion; column (AS4A-SC (manufactured by Dionex Corporation)), eluent (1.8 mM sodium carbonate/1.7 mM sodium hydrogen carbonate), temperature (35° C.).
  Cation; column (CS12A (manufactured by Dionex Corporation)), eluent (20 mM methanesulfonic acid), temperature (35° C.).

The results are shown in Table 1.

TABLE 1

|  | Trade name (Manufacturer's Name) | Membrane material | Filtration pressure (MPa) | Concentration of magnesium sulfate in raw liquid (ppm) | Concentration of magnesium sulfate in permeate (ppm) | Permeation rate of magnesium sulfate (%) |
|---|---|---|---|---|---|---|
| Nanofiltration membrane 1 | UTC60 (TORAY INDUSTRIES, INC.) | Cross-linked piperazine polyamide | 0.5 | 1000 | 2 | 0.2 |
| Nanofiltration membrane 2 | NF-400 (Filmtec Corporation) | Cross-linked piperazine polyamide | 0.5 | 1000 | 20 | 2 |
| Nanofiltration membrane 3 | NF99 (Alfa-Laval) | Polyamide | 0.5 | 1000 | 20 | 2 |
| Nanofiltration membrane 4 | GEsepa (GE Osmonics) | Cellulose acetate | 0.5 | 1000 | 30 | 3 |

(Reference Example 5) Evaluation of Permeability of Citric Acid Through Nanofiltration Membrane To 10 L of ultrapure water, 10 g of citric acid (manufactured by Wako Pure Chemical Industries, Ltd.) was added, and the resulting mixture was stirred at 25° C. for 1 hour, to prepare 1000 ppm aqueous citric acid solution. Subsequently, the permeates from the nanofiltration membranes 1 to 4 were collected under the same conditions as in Reference Example 3. The concentrations of citric acid contained in the raw liquid tank 13 and the permeate 16 were analyzed by high performance liquid chromatography (manufactured by Shimadzu Corporation) under the following conditions, thereby calculating the permeation rate of citric acid and the permeation rate of citric acid/permeation rate of magnesium sulfate.

Column: Shim-Pack SPR-H (manufactured by Shimadzu Corporation); mobile phase: 5 mM p-toluenesulfonic acid (flow rate: 0.8 mL/min.); reaction solution: 5 mM p-toluenesulfonic acid, 20 mM Bis-Tris, 0.1 mM EDTA·2Na (flow rate: 0.8 mL/min); detection method: electric conductivity; temperature: 45° C.

The results are shown in Table 2.

concentrated sulfuric acid (manufactured by Wako Pure Chemical Industries, Ltd.) was then added dropwise to the culture medium to a pH of 1.9 (Reference Example 6), 2.0 (Reference Example 7), 2.2 (Reference Example 8), 2.6 (Reference Examples 9 to 11) or 4.0 (Reference Example 12), followed by stirring the resulting mixture for 1 hour at 25° C., thereby converting calcium lactate in the culture medium into lactic acid and calcium sulfate. Subsequently, precipitated calcium sulfate was separated by filtering precipitates using qualitative filter paper No. 2 (manufactured by ADVANTEC) by suction filtration, and 2 L of the filtrate was collected.

Figure 3:
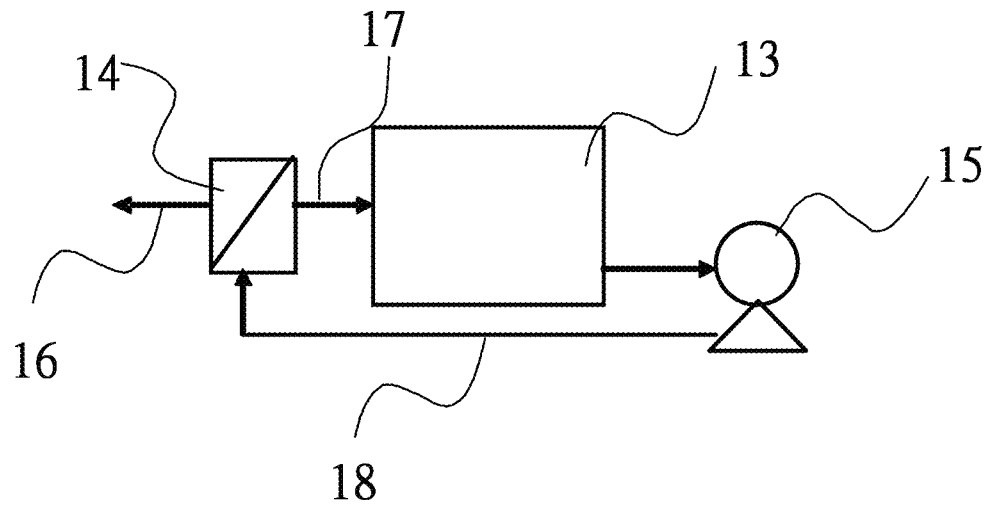
FIG. 3 is a schematic diagram showing an example of the nanofiltration membrane separation apparatus.
Figure 4:
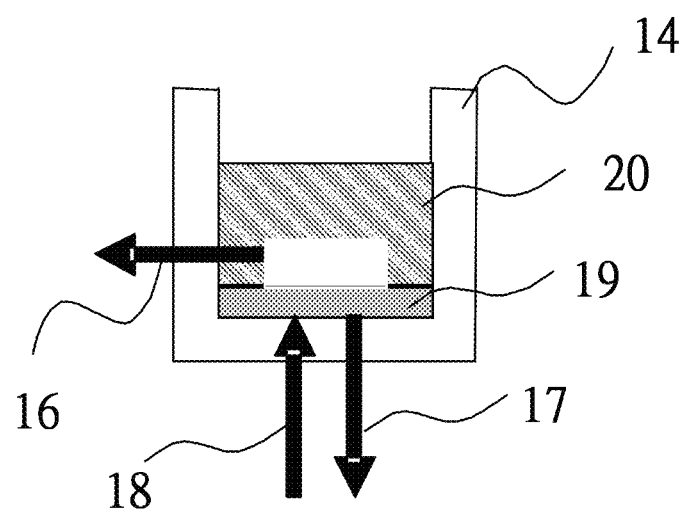
FIG. 4 is a schematic diagram showing an example of the cross-sectional view of the cell in which a nanofiltration membrane was placed, in the nanofiltration membrane separation apparatus.

Subsequently, 2 L of each filtrate obtained as described above was injected into the raw liquid tank 13 of the membrane filtration apparatus shown in FIG. 3. As the 90ϕ nanofiltration membrane indicated by the symbol 19 in FIG. 4, each of the nanofiltration membranes 1 to 4 was placed in a cell made of stainless steel (SUS316). In each case, the pressure of the high-pressure pump 15 was adjusted to 4 MPa to collect the permeate 16. The concentrations of the sulfate ions and the calcium ions contained in the raw liquid tank 13 and the permeate 16 were analyzed by ion chroma-

TABLE 2

| | Trade name (Manufacturer's Name) | Membrane material | Filtration pressure (MPa) | Concentration of citric acid in raw liquid (ppm) | Concentration of citric acid in permeate (ppm) | Permeation rate of citric acid (%) | Permeation rate of citric acid/ permeation rate of magnesium sulfate |
|---|---|---|---|---|---|---|---|
| Nanofiltration membrane 1 | UTC60 (TORAY INDUSTRIES, INC.) | Cross-linked piperazine polyamide | 0.5 | 1000 | 180 | 18 | 70 |
| Nanofiltration membrane 2 | NF-400 (Filmtec Corporation) | Cross-linked piperazine polyamide | 0.5 | 1000 | 140 | 14 | 7 |
| Nanofiltration membrane 3 | NF99 (Alfa-Laval) | Polyamide | 0.5 | 1000 | 160 | 16 | 8 |
| Nanofiltration membrane 4 | GEsepa (GE Osmonics) | Cellulose acetate | 0.5 | 1000 | 60 | 6 | 2 |

(Reference Examples 6 to 12) Permeation Test of Lactic Acid Fermentation Culture Medium Through Nanofiltration Membrane From the culture medium (2L) obtained as in Reference Example 2, cells were removed by centrifugation, and tography (manufactured by Dionex Corporation) under the same conditions as in Reference Example 4, and the lactic acid concentration was analyzed by high performance liquid chromatography (manufactured by Shimadzu Corporation) under the same conditions as in Reference Example 1. The results are shown in Table 3.

TABLE 3

| | Nanofiltration membrane | pH | Membrane permeation flux (m³/m²/d) | Calcium ion concentration | | | Sulfate ion concentration | | | Lactic acid concentration | | |
|---|---|---|---|---|---|---|---|---|---|---|---|---|
| | | | | Raw liquid (mg/L) | Permeate (mg/L) | Removal rate (%) | Raw liquid (mg/L) | Permeate (mg/L) | Removal rate (%) | Raw liquid (mg/L) | Permeate (mg/L) | Removal rate (%) |
| Reference Example 5 | 1 | 1.9 | 2.54 | 557 | 0.8 | 99.9 | 1678 | 428 | 74.5 | 45 | 22.9 | 50.9 |
| Reference Example 6 | 1 | 2 | 2.54 | 557 | 0.8 | 99.9 | 1678 | 428.3 | 74.5 | 45 | 22.9 | 50.9 |
| Reference Example 7 | 1 | 2.2 | 2.5 | 811 | 0.8 | 99.9 | 1165 | 133 | 88.6 | 48 | 24.5 | 51 |
| Reference Example 8 | 1 | 2.6 | 2.5 | 1497 | 1.3 | 99.9 | 918 | 24 | 97.4 | 48 | 24.9 | 51.9 |
| Reference Example 9 | 2 | 2.6 | 2.12 | 1497 | 4.8 | 99.7 | 918 | 26.8 | 97.1 | 48 | 21.2 | 44.2 |
| Reference Example 10 | 3 | 2.6 | 2.08 | 1497 | 6.7 | 99.6 | 918 | 24.3 | 97.4 | 48 | 21.9 | 45.6 |

TABLE 3-continued

| | Nanofiltration membrane | pH | Membrane permeation flux (m³/m²/d) | Calcium ion concentration | | | Sulfate ion concentration | | | Lactic acid concentration | | |
|---|---|---|---|---|---|---|---|---|---|---|---|---|
| | | | | Raw liquid (mg/L) | Permeate (mg/L) | Removal rate (%) | Raw liquid (mg/L) | Permeate (mg/L) | Removal rate (%) | Raw liquid (mg/L) | Permeate (mg/L) | Removal rate (%) |
| Reference Example 11 | 4 | 2.6 | 1.48 | 1497 | 2.1 | 99.9 | 918 | 1.8 | 99.8 | 48 | 21 | 43.8 |
| Reference Example 12 | 1 | 4 | 2.51 | 4909 | 2.9 | 99.9 | 402 | 7.9 | 98 | 49 | 20.9 | 42.7 |

As shown in Table 3, it was revealed that calcium sulfate was removed with high efficiency at all the pHs. It was further revealed that the permeation rate of lactic acid and the membrane permeation flux were highest with the nanofiltration membrane 1.

(Examples 1 to 5) Production Examples of Lactic Acid

To 200 L of the permeate of a porous membrane, which was obtained in Reference Example 3, concentrated sulfuric acid (manufactured by Wako Pure Chemical Industries, Ltd.) was added dropwise to a pH of 1.9 (Example 1), 2.0 (Example 2), 2.2 (Example 3), 2.6 (Example 4) or 4.0 (Example 5), followed by stirring the resulting mixture for 1 hour at 25° C., thereby converting calcium lactate in the culture medium into lactic acid and calcium sulfate. Subsequently, precipitated calcium sulfate was separated by filtering precipitates using qualitative filter paper by suction filtration, and 200 L each of the filtrates was collected.

Subsequently, 200 L of each filtrate obtained in the above Examples was injected into the raw liquid tank 13 of the membrane filtration apparatus shown in FIG. 3. The 4-inch nanofiltration module 2 ("UTC60" manufactured by TORAY INDUSTRIES, INC.) of the nanofiltration membrane 1, which showed the highest lactic acid permeation rates in Reference Examples 6 to 12, was placed in a special vessel, and the operation was carried out by adjusting the pressure of the high-pressure pump 15 to 4 MPa, to collect the permeate at each pH. The concentrations of the sulfuric acid ions and the calcium ions contained in the raw liquid tank 13 and the permeate 16 were analyzed by ion chromatography (manufactured by Dionex Corporation) under the same conditions as in Reference Example 4, and the lactic acid concentration was analyzed by high performance liquid chromatography (manufactured by Shimadzu Corporation) under the same conditions as in Reference Example 1. As a result, it was revealed that calcium sulfate was removed with high efficiency at all the pHs, as in Reference Examples 6 to 12.

Thereafter, 100 L each of the permeates of the nanofiltration membrane was concentrated by distillation of water using a flash evaporator (manufactured by TOKYO RIKAKIKAI) under reduced pressure (50 hPa). At this time, deposition of calcium sulfate was not observed.

Thereafter, distillation was carried out under a reduced pressure of 133 Pa at 130° C. To confirm racemization of the distilled lactic acid, the optical purity was measured before and after the distillation, by high performance liquid chromatography. The results are shown in Table 4.

The obtained purified lactic acid was used for the direct polymerization test in Example 6 and the lactide synthesis test in Example 7, and lactic acid before the distillation was used for the direct polymerization test in Comparative Example 2 and the lactide synthesis test in Comparative Example 3.

(Comparative Example 1) Production Example of Lactic Acid

To 200 L of the membrane permeate obtained as in Reference Example 3, concentrated sulfuric acid (manufactured by Wako Pure Chemical Industries, Ltd.) was added dropwise to a pH of 2.0, followed by stirring the resulting mixture for 1 hour at 25° C., thereby converting calcium lactate in the culture medium into lactic acid and calcium sulfate. Subsequently, precipitated calcium sulfate was separated by filtering precipitates using qualitative filter paper by suction filtration, and 200 L of the filtrate was collected. The concentration of calcium sulfate contained in the filtrate was analyzed by ion chromatography, and the concentration was revealed to be 549 mg/L. Thus, it was revealed that calcium sulfate had not been removed sufficiently.

Thereafter, 100 L of the filtrate was concentrated by distillation of water using a flash evaporator under reduced pressure (50 hPa), and this caused deposition of calcium sulfate that had not been removed by the above-described quality filter paper. Subsequently, distillation was carried out under reduced pressure at 133 Pa, at 130° C. To confirm racemization of the distilled lactic acid, the optical purity of lactic acid was measured before and after the distillation, by high performance liquid chromatography under the same conditions as in Reference Example 1. As a result, decrease in the optical purity was observed. Further, in the distillation residue, partially oligomerized lactic acid was observed, and the distillation yield decreased to 30%. These results are shown in Table 4, together with the results of purification through the nanofiltration membrane.

TABLE 4

| | Optical purity (%) | | Distillation yield |
|---|---|---|---|
| | Before distillation | After distillation | (%) |
| Example 1 | 99.9 | 99.9 | 60 |
| Example 2 | 99.9 | 99.9 | 81 |
| Example 3 | 99.9 | 99.9 | 84 |
| Example 4 | 99.9 | 99.9 | 88 |
| Example 5 | 99.9 | 99.9 | 92 |
| Comparative Example 1 | 99.9 | 94.0 | 30 |

(Example 6) Direct Polymerization Test for Lactic Acid

In a reaction vessel having a stirrer, 150 g of the lactic acid obtained in Example 2 was heated at 800 Pa at 160° C. for 3.5 hours, to obtain oligomers. Subsequently, 0.12 g of tin (II) acetate (manufactured by Kanto Chemical Co., Ltd.) and 0.33 g of methanesulfonic acid (manufactured by Wako Pure Chemical Industries, Ltd.) were added to the oligomers, and the resulting mixture was heated at 500 Pa at 180° C. for 7 hours, to obtain a prepolymer. The prepolymer was then crystallized by heating in an oven at 120° C. for 2 hours. The obtained prepolymer was pulverized using a hammer mill, and made to pass through a sieve, to obtain pulverulent bodies having an average particle size of 0.1 mm. In the solid phase polymerization step, 150 g of the prepolymer was taken, and fed into an oven to which an oil rotary pump was connected, thereby performing vacuum heat treatment. The pressure was set to 50 Pa, and the heating temperature was set to: 140° C. for 10 hours; 150° C. for 10 hours; and 160° C. for 20 hours. The obtained polylactic acid was subjected to weight average molecular weight analysis with GPC (manufactured by Tosoh Corporation), melting point analysis with DSC (manufactured by SII NanoTechnology Inc.) and thermal weight loss rate analysis with TG (manufactured by SII NanoTechnology Inc.).

Weight Average Molecular Weight Analysis of Polylactic Acid

The weight average molecular weight (Mw) of the polylactic acid produced by the polymerization is a value of the weight average molecular weight in terms of the standard polymethyl methacrylate measured by gel permeation chromatography (GPC). The GPC measurement was carried out using HLC8320GPC (manufactured by Tosoh Corporation) as a GPC system, and two TSK-GEL SuperHM-M columns (manufactured by Tosoh Corporation) in series. The detection was carried out using a differential refractometer. In terms of the conditions for the measurement, the flow rate was 0.35 mL/min, hexafluoroisopropanol was used as a solvent, and 0.02 mL of a solution with a sample concentration of 1 mg/mL was injected.

Analysis of Melting Point of Polylactic Acid

The melting point of the polylactic acid produced by the polymerization is a value measured with the differential scanning calorimeter DSC7020 (manufactured by SII NanoTechnology Inc.), and the measurement was carried out with 10 mg of a sample, under nitrogen atmosphere at a heating rate of 20° C./min Analysis of Thermal Weight Loss Rate of Polylactic Acid The thermal weight loss rate of the polylactic acid produced by the polymerization was measured using the thermo gravimetry differential thermal analyzer TG/DTA7200 (manufactured by SII NanoTechnology Inc.). The measurement was carried out with 10 mg of a sample, under nitrogen atmosphere at a constant temperature of 200° C. for a heating time of 20 minutes.

Analysis of Degree of Coloration of Polylactic Acid

In 9.5 g of chloroform, 0.5 g of the polylactic acid produced by the polymerization was dissolved, and the degree of coloration was analyzed using a colorimeter (manufactured by NIPPON DENSHOKU INDUSTRIES CO., LTD.) as an APHA unit color number.

The polylactic acid obtained by direct polymerization of lactic acid had a weight average molecular weight of 155000, melting point of 165° C., thermal weight loss rate of 5% and degree of coloration of APHA 10.

(Comparative Example 2) Test for Direct Polymerization of Lactic Acid

The lactic acid before the distillation in Example 2 was concentrated with a rotary evaporator to 90% by weight, to obtain 150 g of concentrated lactic acid. Direct polymerization was carried out under the same conditions as in Example 6. The polylactic acid obtained by the direct polymerization had a weight average molecular weight of 85000, melting point of 160° C., thermal weight loss rate of 15% and degree of coloration of APHA 50. Thus, the quality of the lactic acid was poorer than that of the lactic acid obtained by Example 6, for all the evaluation items.

(Example 7) Test for Synthesis of Lactide

In a reaction vessel having a stirrer, 150 g of the lactic acid obtained in Example 2 was concentrated by heating under atmospheric pressure at 135° C. for 30 minutes. Subsequently, under reduced pressure (4500 to 6500 Pa), the liquid temperature was increased in a stepwise manner to 135° C. (20 minutes), 150° C. (20 minutes) and 160° C. (20 minutes), to obtain oligomers. Thereafter, 0.75 g of tin (II) octylate (Nacalai Tesque) was added to the oligomers, and simple distillation was carried out under reduced pressure (1000 to 2000 Pa) at 200° C. for 2 hours, to distill lactide. To avoid clogging of pipes, the temperature of the condenser was set to 110° C. A lactide fraction was obtained in an amount of 92.3 g. The yield of lactide was 85.4% based on the starting L-lactic acid.

Analysis of Chemical Purity of Lactide

The chemical purity of the synthesized lactide (ratio of LL-lactide in the recovered lactide) was analyzed with the gas chromatography GC2010 (manufactured by Shimadzu Corporation). As a column, the capillary column RT BDEXM (manufactured by RESTEK) was used, and the measurement conditions were: carrier gas (He) flow rate, 69.2 mL/min; vaporizing chamber temperature, 230° C.; column temperature, 150° C.; detector (FID) temperature, 230° C.; and split ratio, 50. From the peak area ratios of LL-lactide, DD-lactide and DL-lactide, the chemical purity of LL-lactide was calculated.

Analysis of Degree of Coloration of Lactide

Into 20 g of acetone, 6 g of the synthesized lactide was completely dissolved, and the degree of coloration was analyzed using a colorimeter (manufactured by NIPPON DENSHOKU INDUSTRIES CO., LTD.) as an APHA unit color number.

As a result, the obtained lactide had a chemical purity of 96.2% and degree of coloration of APHA 2.

(Comparative Example 3) Test for Synthesis of Lactide

The lactic acid before the distillation in Example 2 was concentrated with a rotary evaporator to 90% by weight, to obtain 150 g of concentrated lactic acid. Lactide was synthesized under the same conditions as in Example 7. The lactide was obtained in an amount of 79.1 g in a yield of 73.2%, and had a chemical purity of 93.1% and degree of coloration of APHA 12. Thus, both the yield and the quality of the lactic acid were poorer than those of the lactic acid obtained by Example 7.

(Example 8) Production of Polylactic Acid by Polymerization Using Lactide as Raw Material, and Evaluation of Physical Properties of Polylactic Acid Into a reaction vessel having a stirrer, 50 g of the lactide obtained in Example 7 and 0.05 g of stearyl alcohol were fed, and the atmosphere inside of the system was replaced with nitrogen, followed by heating the resulting mixture at 190° C. to dissolve the lactide. Subsequently, 0.025 g of tin (II) octylate was added thereto, and polymerization was carried out at 190° C. for 2 hours. The obtained polylactic acid was analyzed for its weight average molecular weight, melting point, thermal weight loss rate and degree of coloration by the methods described in Example 6. The weight average molecular weight was 135000; the melting point was 165° C.; the thermal weight loss rate was 5.1%; and the degree of coloration was APHA 5.

(Comparative Example 4) Production of Polylactic Acid by Polymerization Using Lactide as Raw Material, and Evaluation of Physical Properties of Polylactic Acid Polylactic acid was produced by polymerization of lactide by the same procedure as in Example 8 except that 50 g of the lactide obtained in Comparative Example 3 was used. The obtained polylactic acid had a weight average molecular weight of 109000, melting point of 162° C., weight loss rate of 6.3% and degree of coloration of APHA 11. Thus, the quality of the polylactic acid was poorer than that of the polylactic acid obtained by Example 8, for all the evaluation items.

(Example 9) Analysis of Impurities in Lactic Acid

Three liters of filtrate obtained in the same manner as in Example 3 was filtered through the nanofiltration membrane module SU-610 (manufactured by TORAY INDUSTRIES, INC.) at an operating pressure of 2.0 MPa, to remove impurities. The aqueous lactic acid solution which had permeated through the nanofiltration membrane module was concentrated using the reverse osmosis membrane module SU-810 (manufactured by TORAY INDUSTRIES, INC.), and further concentrated by distillation of water using a rotary evaporator (manufactured by TOKYO RIKAKIKAI) under reduced pressure (50 hPa), thereby obtaining 80% aqueous lactic acid solution. Subsequently, distillation was carried out under a reduced pressure of 133 Pa at 133° C., to obtain 500 g of lactic acid.

Analysis of Impurities in Lactic Acid

To the lactic acid obtained as described above, pure water was added to prepare 90% aqueous lactic acid solution. Impurities contained were analyzed by HPLC (high performance liquid chromatography) or GC (gas chromatography) under the following conditions. The results of the analysis are shown in Table 5.

Analysis of Acetic Acid, Pyruvic Acid and 2-Hydroxybutyric Acid by HPLC
  Column: Shim-Pack SPR-H (manufactured by Shimadzu Corporation); mobile phase: 5 mM p-toluenesulfonic acid (flow rate: 0.8 mL/min.); reaction solution: 5 mM p-toluenesulfonic acid, 20 mM Bis-Tris, 0.1 mM EDTA·2Na (flow rate: 0.8 mL/min); detection method: electric conductivity; temperature: 45° C.
Analysis of Furfural and HMF by HPLC
  Column: Synergie HydroRP (manufactured by Phenomenex, Inc.); mobile phase: 5% aqueous acetonitrile solution (flow rate 1.0 mL/min); detection method: UV (283 nm); temperature: 40° C.
Analysis of Methanol and Methyl Lactate by GC Method
  Column: DB-5 (0.25 mm×30 m, manufactured by J&W); column temperature: 50° C. to 250° C. (8° C./min); inlet temperature: 250° C.; carrier gas: helium; carrier pressure: 65 kPa.

As shown in table 5, the concentrations of all the impurities other than acetic acid and pyruvic acid were 0 ppm (below the detection limit).

TABLE 5

| Name of impurity | Content in 90% lactic acid |
| --- | --- |
| Methanol | 0 ppm |
| Acetic acid | 200 ppm |
| Pyruvic acid | 200 ppm |
| 2-Hydroxybutyric acid | 0 ppm |
| Furfural | 0 ppm |
| 5-Hydroxymethylfurfural | 0 ppm |
| Methyl lactate | 0 ppm |

(Example 10) Test for Direct Polymerization of Lactic Acid, and Evaluation of Physical Properties of Polylactic Acid In a reaction vessel having a stirrer, 150 g of the 90% aqueous lactic acid solution in Example 9 was heated at 800 Pa at 160° C. for 3.5 hours, to obtain oligomers. Subsequently, 0.12 g of tin (II) acetate (manufactured by Kanto Chemical Co., Ltd.) and 0.33 g of methanesulfonic acid (manufactured by Wako Pure Chemical Industries, Ltd.) were added to the oligomers, and the resulting mixture was heated at 500 Pa at 180° C. for 7 hours, to obtain a prepolymer. The prepolymer was then crystallized by heating in an oven at 120° C. for 2 hours. The obtained prepolymer was pulverized using a hammer mill, and made to pass through a sieve, to obtain pulverulent bodies having an average particle size of 0.1 mm. In the solid phase polymerization step, 150 g of the prepolymer was taken, and fed into an oven to which an oil rotary pump was connected, thereby performing vacuum heat treatment. The pressure was set to 50 Pa, and the heating temperature was set to: 140° C. for 10 hours; 150° C. for 10 hours; and 160° C. for 20 hours. The weight average molecular weight, melting point, thermal weight loss rate and degree of coloration of the obtained polylactic acid were analyzed by the methods described in Example 6.

(Example 11) Analysis of Impurities in Lactic Acid, Test for Direct Polymerization of Lactic Acid, and Evaluation of Physical Properties of Polylactic Acid Polylactic acid was produced by polymerization and analyzed in the same manner as in Example 10 except that 150 g of an aqueous lactic acid solution was used, which aqueous lactic acid solution was prepared by adding the respective components, among the impurities contained in the 90% aqueous lactic acid solution obtained in Example 9, to the lactic acid obtained in Example 9 such that their concentrations were adjusted to 30 ppm methanol, 100 ppm formic acid, 200 ppm pyruvic acid, 100 ppm 2-hydroxybutyric acid, 3 ppm furfural, 2 ppm 5-hydroxymethylfurfural and 100 ppm methyl lactate.

(Example 12) Analysis of Impurities in Lactic Acid, Test for Direct Polymerization of Lactic Acid, and Evaluation of Physical Properties of Polylactic Acid Polylactic acid was produced by polymerization and analyzed in the same manner as in Example 10 except that 150 g of an aqueous lactic acid solution was used, which aqueous lactic acid solution was prepared by adding the respective components, among the impurities contained in the 90% aqueous lactic acid solution obtained in Example 9, to the lactic acid obtained in Example 9 such that their concentrations were adjusted to 65 ppm methanol, 100 ppm formic acid, 300 ppm acetic acid, 300 ppm pyruvic acid, 150 ppm 2-hydroxybutyric acid, 5 ppm furfural, 5 ppm 5-hydroxymethylfurfural and 350 ppm methyl lactate.

(Comparative Example 5) Analysis of Impurities in Lactic Acid and Evaluation of Physical Properties of Polylactic Acid Polylactic acid was produced by polymerization and analyzed in the same manner as in Example 10 except that 150 g of an aqueous lactic acid solution was used, which aqueous lactic acid solution was prepared by adding the respective components, among the impurities contained in the 90% aqueous lactic acid solution obtained in Example 9, to the lactic acid obtained in Example 9 such that their concentrations were adjusted to 100 ppm methanol, 100 ppm formic acid, 300 ppm acetic acid, 300 ppm pyruvic acid, 150 ppm 2-hydroxybutyric acid, 5 ppm furfural, 5 ppm 5-hydroxymethylfurfural and 350 ppm methyl lactate.

(Comparative Example 6) Analysis of Impurities in Lactic Acid, Test for Direct Polymerization of Lactic Acid, and Evaluation of Physical Properties of Polylactic Acid Polylactic acid was produced by polymerization and analyzed in the same manner as in Example 10 except that 150 g of an aqueous lactic acid solution was used, which aqueous lactic acid solution was prepared by adding the respective components, among the impurities contained in the 90% aqueous lactic acid solution obtained in Example 9, to the lactic acid obtained in Example 9 such that their concentrations were adjusted to 65 ppm methanol, 100 ppm formic acid, 300 ppm acetic acid, 600 ppm pyruvic acid, 150 ppm 2-hydroxybutyric acid, 5 ppm furfural, 5 ppm 5-hydroxymethylfurfural and 350 ppm methyl lactate.

(Comparative Example 7) Analysis of Impurities in Lactic Acid, Test for Direct Polymerization of Lactic Acid, and Evaluation of Physical Properties of Polylactic Acid Polylactic acid was produced by polymerization and analyzed in the same manner as in Example 10 except that 150 g of an aqueous lactic acid solution was used, which aqueous lactic acid solution was prepared by adding the respective components, among the impurities contained in the 90% aqueous lactic acid solution obtained in Example 9, to the lactic acid obtained in Example 9 such that their concentrations were adjusted to 65 ppm methanol, 100 ppm formic acid, 300 ppm acetic acid, 300 ppm pyruvic acid, 150 ppm 2-hydroxybutyric acid, 5 ppm furfural, 25 ppm 5-hydroxymethylfurfural and 350 ppm methyl lactate.

(Comparative Example 8) Analysis of Impurities in Lactic Acid, Test for Direct Polymerization of Lactic Acid, and Evaluation of Physical Properties of Polylactic Acid Polylactic acid was produced by polymerization and analyzed in the same manner as in Example 10 except that 150 g of an aqueous lactic acid solution was used, which aqueous lactic acid solution was prepared by adding the respective components, among the impurities contained in the 90% aqueous lactic acid solution obtained in Example 9, to the lactic acid obtained in Example 9 such that their concentrations were adjusted to 65 ppm methanol, 100 ppm formic acid, 300 ppm acetic acid, 300 ppm pyruvic acid, 150 ppm 2-hydroxybutyric acid, 25 ppm furfural, 5 ppm 5-hydroxymethylfurfural and 350 ppm methyl lactate.

(Comparative Example 9) Analysis of Impurities in Lactic Acid, Test for Direct Polymerization of Lactic Acid, and Evaluation of Physical Properties of Polylactic Acid Polylactic acid was produced by polymerization and analyzed in the same manner as in Example 10 except that 150 g of an aqueous lactic acid solution was used, which aqueous lactic acid solution was prepared by adding the respective components, among the impurities contained in the 90% aqueous lactic acid solution obtained in Example 9, to the lactic acid obtained in Example 9 such that their concentrations were adjusted to 65 ppm methanol, 100 ppm formic acid, 300 ppm acetic acid, 300 ppm pyruvic acid, 150 ppm 2-hydroxybutyric acid, 5 ppm furfural, 5 ppm 5-hydroxymethylfurfural and 650 ppm methyl lactate.

(Comparative Example 10) Analysis of Impurities in Lactic Acid, Test for Direct Polymerization of Lactic Acid, and Evaluation of Physical Properties of Polylactic Acid Polylactic acid was produced by polymerization and analyzed in the same manner as in Example 10 except that 150 g of an aqueous lactic acid solution was used, which aqueous lactic acid solution was prepared by adding the respective components, among the impurities contained in the 90% aqueous lactic acid solution obtained in Example 9, to the lactic acid obtained in Example 9 such that their concentrations were adjusted to 70 ppm methanol, 750 ppm 2-hydroxybutyric acid and 500 ppm methyl lactate.

(Comparative Example 11) Analysis of Impurities in Lactic Acid, Test for Direct Polymerization of Lactic Acid, and Evaluation of Physical Properties of Polylactic Acid Polylactic acid was produced by polymerization and analyzed in the same manner as in Example 10 except that 150 g of an aqueous lactic acid solution was used, which aqueous lactic acid solution was prepared by adding the respective components, among the impurities contained in the 90% aqueous lactic acid solution obtained in Example 9, to the lactic acid obtained in Example 9 such that their concentrations were adjusted to 600 ppm acetic acid and 300 ppm pyruvic acid.

The weight average molecular weights, melting points, thermal weight loss rates and degrees of coloration APHA of the polylactic acids obtained in Examples 10 to 12 and Comparative Examples 5 to 11 are shown in Table 6. In Examples 10 to 12, polylactic acids having excellent physical properties for the weight average molecular weight, thermal weight loss rate and degree of coloration were obtained. However, in Comparative Example 5, the weight average molecular weight was small and hence the mechanical strength was low, and the thermal weight loss rate was high and hence the thermal stability was low; in Comparative Examples 6 to 9, the thermal weight loss rate was high and the degree of coloration was high; and in Comparative Examples 10 and 11, the thermal weight loss rate was high. From these results, it was revealed that, in cases where the amounts of the impurities in lactic acid are not more than predetermined values, polylactic acid having excellent thermal stability, mechanical strength and hue can be obtained.

(Example 13) Analysis of Impurities in Lactic Acid, and Evaluation of Physical Properties of Lactide In a reaction vessel having a stirrer, 150 g of the lactic acid obtained in Example 9 was concentrated under heat at 135° C. under atmospheric pressure for 30 minutes. Subsequently, under reduced pressure (4500 to 6500 Pa), the liquid temperature was increased in a stepwise manner to 135° C. (20 minutes), 150° C. (20 minutes) and 160° C. (20 minutes), to obtain oligomers. Thereafter, 0.75 g of tin (II) octylate (Nacalai Tesque) was added to the oligomers, and simple distillation was carried out under reduced pressure (1000 to 2000 Pa) at 200° C. for 2 hours, to distill lactide. To avoid clogging of pipes, the temperature of the condenser was set to 110° C. A lactide fraction was obtained in an amount of 93.3 g. The yield of lactide was 87.2% based on the starting L-lactic acid.

(Example 14) Analysis of Impurities in Lactic Acid, and Evaluation of Physical Properties of Lactide Lactide was synthesized in the same manner as in Example 13 except that 150 g of an aqueous lactic acid solution was used, which aqueous lactic acid solution was prepared by adding the respective components, among the impurities contained in the 90% aqueous lactic acid solution obtained in Example 9, to the lactic acid obtained in Example 9 such that their concentrations were adjusted to 30 ppm methanol, 100 ppm formic acid, 200 ppm pyruvic acid, 100 ppm 2-hydroxybutyric acid, 3 ppm furfural, 2 ppm 5-hydroxymethylfurfural and 100 ppm methyl lactate.

(Example 15) Analysis of Impurities in Lactic Acid, and Evaluation of Physical Properties of Lactide Lactide was synthesized in the same manner as in Example 13 except that 150 g of an aqueous lactic acid solution was used, which aqueous lactic acid solution was prepared by adding the respective components, among the impurities contained in the 90% aqueous lactic acid solution obtained in Example 9, to the lactic acid obtained in Example 9 such that their concentrations were adjusted to 65 ppm methanol, 100 ppm formic acid, 300 ppm acetic acid, 300 ppm pyruvic acid, 150 ppm 2-hydroxybutyric acid, 5 ppm furfural, 5 ppm 5-hydroxymethylfurfural and 350 ppm methyl lactate.

(Comparative Example 12) Analysis of Impurities in Lactic Acid, and Evaluation of Physical Properties of Lactide Lactide was synthesized in the same manner as in Example 13 except that 150 g of an aqueous lactic acid solution was used, which aqueous lactic acid solution was prepared by adding the respective components, among the impurities contained in the 90% aqueous lactic acid solution obtained in Example 9, to the lactic acid obtained in Example 9 such that their concentrations were adjusted to 100 ppm methanol, 100 ppm formic acid, 300 ppm acetic acid, 300 ppm pyruvic acid, 150 ppm 2-hydroxybutyric acid, 5 ppm furfural, 5 ppm 5-hydroxymethylfurfural and 350 ppm methyl lactate.

(Comparative Example 13) Analysis of Impurities in Lactic Acid, and Evaluation of Physical Properties of Lactide Lactide was synthesized in the same manner as in Example 13 except that 150 g of an aqueous lactic acid solution was used, which aqueous lactic acid solution was prepared by adding the respective components, among the impurities contained in the 90% aqueous lactic acid solution obtained in Example 9, to the lactic acid obtained in Example 9 such that their concentrations were adjusted to 65 ppm methanol, 100 ppm formic acid, 300 ppm acetic acid, 600 ppm pyruvic acid, 150 ppm 2-hydroxybutyric acid, 5 ppm furfural, 5 ppm 5-hydroxymethylfurfural and 350 ppm methyl lactate.

(Comparative Example 14) Analysis of Impurities in Lactic Acid, and Evaluation of Physical Properties of Lactide Lactide was synthesized in the same manner as in Example 13 except that 150 g of an aqueous lactic acid solution was used, which aqueous lactic acid solution was prepared by adding the respective components, among the impurities contained in the 90% aqueous lactic acid solution obtained in Example 9, to the lactic acid obtained in Example 9 such that their concentrations were adjusted to 65 ppm methanol, 100 ppm formic acid, 300 ppm acetic acid, 300 ppm pyruvic acid, 150 ppm 2-hydroxybutyric acid, 5 ppm furfural, 25 ppm 5-hydroxymethylfurfural and 350 ppm methyl lactate.

(Comparative Example 15) Analysis of Impurities in Lactic Acid, and Evaluation of Physical Properties of Lactide Lactide was synthesized in the same manner as in Example 13 except that 150 g of an aqueous lactic acid solution was used, which aqueous lactic acid solution was prepared by adding the respective components, among the impurities contained in the 90% aqueous lactic acid solution obtained in Example 9, to the lactic acid obtained in Example 9 such that their concentrations were adjusted to 65 ppm methanol, 100 ppm formic acid, 300 ppm acetic acid, 300 ppm pyruvic acid, 150 ppm 2-hydroxybutyric acid, 25 ppm furfural, 5 ppm 5-hydroxymethylfurfural and 350 ppm methyl lactate.

(Comparative Example 16) Analysis of Impurities in Lactic Acid, and Evaluation of Physical Properties of Lactide Lactide was synthesized in the same manner as in Example 13 except that 150 g of an aqueous lactic acid solution was used, which aqueous lactic acid solution was prepared by adding the respective components, among the impurities contained in the 90% aqueous lactic acid solution obtained in Example 9, to the lactic acid obtained in Example 9 such that their concentrations were adjusted to 65 ppm methanol, 100 ppm formic acid, 300 ppm acetic acid, 300 ppm pyruvic acid, 150 ppm 2-hydroxybutyric acid, 5 ppm furfural, 5 ppm 5-hydroxymethylfurfural and 650 ppm methyl lactate.

(Comparative Example 17) Analysis of Impurities in Lactic Acid, and Evaluation of Physical Properties of Lactide Lactide was synthesized in the same manner as in Example 13 except that 150 g of an aqueous lactic acid solution was used, which aqueous lactic acid solution was prepared by adding the respective components, among the impurities contained in the 90% aqueous lactic acid solution obtained in Example 9, to the lactic acid obtained in Example 9 such that their concentrations were adjusted to 70 ppm methanol, 750 ppm 2-hydroxybutyric acid and 500 ppm methyl lactate.

(Comparative Example 18) Analysis of Impurities in Lactic Acid, and Evaluation of Physical Properties of Lactide Lactide was produced by polymerization in the same manner as in Example 13 except that 150 g of an aqueous lactic acid solution was used, which aqueous lactic acid solution was prepared by adding the respective components, among the impurities contained in the 90% aqueous lactic acid solution obtained in Example 9, to the lactic acid obtained in Example 9 such that their concentrations were adjusted to 600 ppm acetic acid and 300 ppm pyruvic acid.

The yields and the degrees of coloration APHA of the lactides obtained in Examples 13 to 15 and Comparative Examples 12 to 18 are shown in Table 6. In Examples 13 to 15, excellent results were obtained for the yield of lactide and the degree of coloration. However, in Comparative Examples 12 to 18, the yield was less than 80%; and in Comparative Examples 13 to 15, wherein large amounts of pyruvic acid, furfural and the like were contained, the degree of coloration was high. From these results, it was revealed that, in cases where the amounts of the impurities in lactic acid are not more than predetermined values, lactide showing a high yield and a low degree of coloration can be obtained.

(Example 16) Production of Polylactic Acid by Polymerization Using Lactide as Raw Material, and Evaluation of Physical Properties of Polylactic Acid Into a reaction vessel having a stirrer, 50 g of the lactide obtained in Example 13 and 0.05 g of stearyl alcohol were fed, and the atmosphere inside of the system was replaced with nitrogen, followed by heating the resulting mixture at 190° C. to dissolve the lactide. Subsequently, 0.025 g of tin (II) octylate was added thereto as a catalyst, and polymerization was carried out at 190° C. for 2 hours. The obtained polylactic acid was analyzed for its weight average molecular weight, melting point, thermal weight loss rate and degree of coloration by the methods described in Example 6.

(Example 17) Production of Polylactic Acid by Polymerization Using Lactide as Raw Material, and Evaluation of Physical Properties of Polylactic Acid Polylactic acid was produced by polymerization of lactide, and analyzed, by the same procedure as in Example 16 except that 50 g of the lactide obtained in Example 14 was used.

(Example 18) Production of Polylactic Acid by Polymerization Using Lactide as Raw Material, and Evaluation of Physical Properties of Polylactic Acid Polylactic acid was produced by polymerization of lactide, and analyzed, by the same procedure as in Example 16 except that 50 g of the lactide obtained in Example 15 was used.

(Comparative Example 19) Production of Polylactic Acid by Polymerization Using Lactide as Raw Material, and Evaluation of Physical Properties of Polylactic Acid Polylactic acid was produced by polymerization of lactide, and analyzed, by the same procedure as in Example 16 except that 50 g of the lactide obtained in Comparative Example 12 was used.

(Comparative Example 20) Production of Polylactic Acid by Polymerization Using Lactide as Raw Material, and Evaluation of Physical Properties of Polylactic Acid Polylactic acid was produced by polymerization of lactide, and analyzed, by the same procedure as in Example 16 except that 50 g of the lactide obtained in Comparative Example 13 was used.

(Comparative Example 21) Production of Polylactic Acid by Polymerization Using Lactide as Raw Material, and Evaluation of Physical Properties of Polylactic Acid Polylactic acid was produced by polymerization of lactide, and analyzed, by the same procedure as in Example 16 except that 50 g of the lactide obtained in Comparative Example 14 was used.

(Comparative Example 22) Production of Polylactic Acid by Polymerization Using Lactide as Raw Material, and Evaluation of Physical Properties of Polylactic Acid Polylactic acid was produced by polymerization of lactide, and analyzed, by the same procedure as in Example 16 except that 50 g of the lactide obtained in Comparative Example 15 was used.

(Comparative Example 23) Production of Polylactic Acid by Polymerization Using Lactide as Raw Material, and Evaluation of Physical Properties of Polylactic Acid Polylactic acid was produced by polymerization of lactide, and analyzed, by the same procedure as in Example 16 except that 50 g of the lactide obtained in Comparative Example 16 was used.

(Comparative Example 24) Production of Polylactic Acid by Polymerization Using Lactide as Raw Material, and Evaluation of Physical Properties of Polylactic Acid Polylactic acid was produced by polymerization of lactide, and analyzed, by the same procedure as in Example 16 except that 50 g of the lactide obtained in Comparative Example 17 was used.

(Comparative Example 25) Production of Polylactic Acid by Polymerization Using Lactide as Raw Material, and Evaluation of Physical Properties of Polylactic Acid Polylactic acid was produced by polymerization of lactide, and analyzed, by the same procedure as in Example 16 except that 50 g of the lactide obtained in Comparative Example 18 was used.

The weight average molecular weights, melting points, thermal weight loss rates and degrees of coloration APHA of the polylactic acids obtained in Examples 16 to 18 and Comparative Examples 19 to 25 are shown in Table 6. In Examples 16 to 18, polylactic acids having excellent physical properties for the weight average molecular weight, thermal weight loss rate and degree of coloration were obtained. However, in Comparative Examples 19 and 20, the weight average molecular weight was small. Further, in Comparative Examples 20 to 22, the weight loss rate was high and the degree of coloration was high; and in Comparative Examples 23 to 25, the weight loss rate was high.

TABLE 6

| | Lactic acid | Example 10 | Example 11 | Example 12 | Comparative Example 5 | Comparative Example 6 | Comparative Example 7 | Comparative Example 8 | Comparative Example 9 | Comparative Example 10 | Comparative Example 11 |
|---|---|---|---|---|---|---|---|---|---|---|---|
| Impurity contents (ppm) | Methanol | 0 | 30 | 65 | 100 | 65 | 65 | 65 | 65 | 70 | 0 |
| | Acetic acid | 200 | 200 | 300 | 300 | 300 | 300 | 300 | 300 | 0 | 600 |
| | Pyruvic acid | 200 | 200 | 300 | 300 | 600 | 300 | 300 | 300 | 200 | 200 |
| | 2-Hydroxybutyric acid | 0 | 100 | 150 | 150 | 150 | 150 | 150 | 150 | 750 | 0 |
| | Furfural | 0 | 3 | 5 | 5 | 5 | 5 | 25 | 5 | 0 | 0 |
| | 5-Hydroxymethylfurfural | 0 | 2 | 5 | 5 | 5 | 25 | 5 | 5 | 0 | 0 |
| | Methyl lactate | 0 | 100 | 350 | 350 | 350 | 350 | 350 | 650 | 500 | 0 |
| Evaluation results of direct polymerization | Weight average molecular weight (Mw) | 175000 | 156000 | 145000 | 115000 | 128000 | 153000 | 144000 | 118000 | 149000 | 161000 |
| | Melting point (° C.) | 167 | 165 | 164 | 163 | 164 | 165 | 163 | 162 | 162 | 165 |
| | Weight loss rate (%) | 4.9 | 5.5 | 5.9 | 6.7 | 8.5 | 8.6 | 7.9 | 6.5 | 6.5 | 6.7 |
| | Degree of coloration (APHA) | 7 | 10 | 15 | 16 | 25 | 40 | 20 | 25 | 7 | 8 |

| | Lactide | Example 13 | Example 14 | Example 15 | Comparative Example 12 | Comparative Example 13 | Comparative Example 14 | Comparative Example 15 | Comparative Example 16 | Comparative Example 17 | Comparative Example 18 |
|---|---|---|---|---|---|---|---|---|---|---|---|
| Evaluation of lactide | Yield (%) | 85 | 81 | 80 | 78 | 73 | 75 | 76 | 75 | 77 | 75 |
| | Degree of coloration (APHA) | 2 | 2 | 6 | 8 | 12 | 10 | 10 | 10 | 6 | 6 |

| | Polymerization of polylactic acid from lactide | Example 16 | Example 17 | Example 18 | Comparative Example 19 | Comparative Example 20 | Comparative Example 21 | Comparative Example 22 | Comparative Example 23 | Comparative Example 24 | Comparative Example 25 |
|---|---|---|---|---|---|---|---|---|---|---|---|
| Results of evaluation of polymerization | Weight average molecular weight (Mw) | 135000 | 133000 | 122000 | 118000 | 109000 | 124000 | 123000 | 130000 | 129000 | 131000 |
| | Melting point (° C.) | 165 | 164 | 162 | 162 | 162 | 163 | 162 | 163 | 162 | 163 |
| | Weight loss rate (%) | 5.1 | 5.3 | 6.2 | 6.0 | 6.3 | 7.4 | 7.0 | 7.2 | 7.5 | 7.3 |
| | Degree of coloration (APHA) | 5 | 6 | 8 | 8 | 11 | 14 | 12 | 9 | 8 | 9 |

INDUSTRIAL APPLICABILITY

The lactic acid obtained by our method for producing lactic acid can be suitably used for food and pharmaceuticals, and as a monomer material for polylactic acid, which is a biodegradable general-purpose plastic. Further, polylactic acid obtained by using the lactic acid as a raw material has excellent thermal stability, mechanical strength and hue, so that the polylactic acid is suitable for various uses such as fibers, films and molded articles.

What is claimed is:

1. A purified lactic acid composition comprising lactic acid having optical purity of not less than 95%,
   wherein the lactic acid composition contains methanol at a concentration of not more than 0.007778 wt % (weight/lactic acid weight), pyruvic acid at a concentration of 0.022222 to 0.05556 wt % (weight/lactic acid weight), furfural at a concentration of 0.0003333 to 0.001667 (weight/lactic acid weight), 5-hydroxymethylfurfural at a concentration of 0.00022222 to 0.001667 wt % (weight/lactic acid weight), methyl lactate at a concentration of not more than 0.04444 wt % (weight/lactic acid weight), acetic acid at a concentration of not more than 0.04444 wt % (weight/lactic acid weight), and 2-hydroxybutyric acid at a concentration of 0.011111 to 0.02222 wt % (weight/lactic acid weight).

2. The purified lactic acid composition according to claim 1, having an optical purity of not less than 99%.

3. The purified lactic acid composition according to claim 1, wherein the purified lactic acid composition contains acetic acid at a concentration of 0.022222 to 0.04444 wt % (weight/lactic acid weight).

4. The purified lactic acid composition according to claim 1, wherein the lactic acid composition yields a polylactic acid having an American Public Health Association (APHA) unit color number of not more than 15 after polymerization.

5. A purified lactic acid composition comprising lactic acid having optical purity of not less than 95%,
   wherein the lactic acid composition contains methanol at a concentration of not more than 0.007778 wt % (weight/lactic acid weight), pyruvic acid at a concentration of not more than 0.05556 wt % (weight/lactic acid weight), furfural at a concentration of not more than 0.001667 wt % (weight/lactic acid weight), 5-hydroxymethylfurfural at a concentration of not more than 0.001667 wt % (weight/lactic acid weight), methyl lactate at a concentration of not more than 0.04444 wt % (weight/lactic acid weight), acetic acid at a concentration of not more than 0.04444 wt % (weight/lactic acid weight), and 2-hydroxybutyric acid at a concentration of more than 0.02222 wt % (weight/lactic acid weight).

6. The purified lactic acid composition according to claim 5, wherein the lactic acid composition yields a polylactic acid having an American Public Health Association (APHA) unit color number of not more than 15 after polymerization.

* * * * *